(12) United States Patent
Childers et al.

(10) Patent No.: US 8,323,231 B2
(45) Date of Patent: Dec. 4, 2012

(54) METHOD AND APPARATUS FOR MONITORING AND CONTROLLING PERITONEAL DIALYSIS THERAPY

(75) Inventors: Robert Warren Childers, New Port Richey, FL (US); Vital Eerlingen, Leuven (BE); Patrick Balteau, Bothey (BE); Duane Belongie, Minneapolis, MN (US)

(73) Assignee: Baxter International, Inc., Deerfield, IL (US)

( * ) Notice: Subject to any disclaimer, the term of this patent is extended or adjusted under 35 U.S.C. 154(b) by 28 days.

(21) Appl. No.: 11/617,543

(22) Filed: Dec. 28, 2006

(65) Prior Publication Data

US 2007/0135758 A1 Jun. 14, 2007

Related U.S. Application Data

(60) Continuation of application No. 10/446,068, filed on May 27, 2003, now Pat. No. 7,507,220, and a division of application No. 10/078,568, filed on Feb. 14, 2002, now Pat. No. 6,592,542, and a continuation of application No. 09/501,778, filed on Feb. 10, 2000, now Pat. No. 6,497,676.

(51) Int. Cl.
  *A61M 1/00* (2006.01)
  *A61M 31/00* (2006.01)
(52) U.S. Cl. .................. 604/30; 604/29; 604/67
(58) Field of Classification Search .......... 604/30, 604/29, 111, 31, 65–67, 131; 417/477.2
  See application file for complete search history.

(56) References Cited

U.S. PATENT DOCUMENTS

| | | | |
|---|---|---|---|
| 2,286,613 A | 1/1942 | Fuller | |
| 2,705,223 A | 3/1955 | Renfrew et al. | |
| 2,971,876 A | 2/1961 | Phair | |
| 3,255,923 A | 6/1966 | Soto | |
| 3,327,115 A | 6/1967 | Barlett | |
| 3,375,300 A | 3/1968 | Ropp | |
| 3,428,828 A | 2/1969 | Korzekwa et al. | |
| 3,485,245 A | 12/1969 | Lahr et al. | |
| 3,494,897 A | 2/1970 | Reding et al. | |
| 3,507,708 A | 4/1970 | Vingnaud | |

(Continued)

FOREIGN PATENT DOCUMENTS

DE   1964735   7/1971

(Continued)

OTHER PUBLICATIONS

Durand, P. et al., APD: Clinical Measurement of the Maximal Acceptable Intraperitoneal Volume, *Advances in Peritoneal Dialysis*, vol. 10, 1994, pp. 63-67.

(Continued)

*Primary Examiner* — Kevin C. Sirmons
*Assistant Examiner* — Michael J Anderson
(74) *Attorney, Agent, or Firm* — K&L Gates LLP

(57) ABSTRACT

A peritoneal dialysis system includes: (i) a fluid cassette including diaphragm operated first and second pump chambers; (ii) a first pressure sensor operable with the first pump chamber; (iii) a second pressure sensor operable with the second pump chamber; and (iv) a to-patient port of the cassette in fluid communication with the first and second pump chambers, wherein the first pressure sensor is located between the first pump chamber and the to-patient port and the second pressure sensor is located between the second pump chamber and the to-patient port.

25 Claims, 8 Drawing Sheets

U.S. PATENT DOCUMENTS

| | | |
|---|---|---|
| 3,514,359 A | 5/1970 | Frese |
| 3,561,493 A | 2/1971 | Maillard |
| 3,620,215 A | 11/1971 | Tysk et al. |
| 3,626,670 A | 12/1971 | Pecker |
| 3,645,992 A | 2/1972 | Elston |
| 3,656,873 A | 4/1972 | Schiff |
| 3,689,204 A | 9/1972 | Prisk |
| 3,703,959 A | 11/1972 | Raymond |
| 3,707,967 A | 1/1973 | Kitrilakis et al. |
| 3,709,222 A | 1/1973 | Devries |
| 3,772,136 A | 11/1973 | Workman |
| 3,792,643 A | 2/1974 | Scheafer |
| 3,814,799 A | 6/1974 | Wygasch |
| 3,816,033 A | 6/1974 | Fried et al. |
| 3,858,581 A | 1/1975 | Kamen |
| 3,902,490 A | 9/1975 | Jacobsen |
| 3,912,843 A | 10/1975 | Brazier |
| 3,937,758 A | 2/1976 | Castagna |
| 3,955,901 A | 5/1976 | Hamilton |
| 3,976,574 A | 8/1976 | White |
| 3,979,284 A | 9/1976 | Granger |
| 3,995,084 A | 11/1976 | Berger et al. |
| 4,041,103 A | 8/1977 | Davison et al. |
| 4,058,647 A | 11/1977 | Inoue et al. |
| 4,071,040 A | 1/1978 | Moriarty |
| 4,086,653 A | 4/1978 | Gernes |
| 4,087,587 A | 5/1978 | Shida et al. |
| 4,087,588 A | 5/1978 | Shida et al. |
| 4,095,012 A | 6/1978 | Schirmer |
| 4,096,859 A | 6/1978 | Agarwal et al. |
| 4,110,303 A | 8/1978 | Gergen et al. |
| 4,122,947 A | 10/1978 | Falla |
| 4,126,132 A | 11/1978 | Portner et al. |
| 4,137,915 A | 2/1979 | Kamen |
| 4,140,118 A | 2/1979 | Jassawalla |
| 4,142,524 A | 3/1979 | Jassawalla et al. |
| 4,147,827 A | 4/1979 | Breidt, Jr. et al. |
| 4,158,530 A | 6/1979 | Bernstein |
| 4,181,245 A | 1/1980 | Garrett et al. |
| 4,184,497 A | 1/1980 | Kolff et al. |
| 4,187,057 A | 2/1980 | Xanthopoulos |
| 4,199,307 A | 4/1980 | Jassawalla |
| 4,211,519 A | 7/1980 | Hogan |
| 4,233,367 A | 11/1980 | Ticknor et al. |
| 4,235,231 A | 11/1980 | Schindler et al. |
| 4,236,880 A | 12/1980 | Archibald |
| 4,239,041 A | 12/1980 | Popovich et al. |
| 4,240,408 A | 12/1980 | Schael |
| 4,243,619 A | 1/1981 | Fraser et al. |
| 4,252,651 A | 2/1981 | Soderstrom |
| 4,265,601 A | 5/1981 | Mandroian |
| 4,273,121 A | 6/1981 | Jassawalla |
| 4,277,226 A | 7/1981 | Archibald |
| 4,286,597 A | 9/1981 | Gajewski |
| 4,298,714 A | 11/1981 | Levin et al. |
| 4,303,376 A | 12/1981 | Siekmann |
| 4,306,976 A | 12/1981 | Bazzato |
| 4,310,141 A | 1/1982 | Tamura |
| 4,316,466 A | 2/1982 | Babb |
| 4,322,465 A | 3/1982 | Webster |
| 4,322,480 A | 3/1982 | Tuller et al. |
| D264,134 S | 4/1982 | Xanthopoulos |
| 4,327,726 A | 5/1982 | Kwong et al. |
| 4,332,655 A | 6/1982 | Berejka |
| 4,333,088 A | 6/1982 | Diggins |
| 4,336,352 A | 6/1982 | Sakurai et al. |
| 4,338,190 A | 7/1982 | Kraus et al. |
| 4,351,333 A | 9/1982 | Lazarus et al. |
| 4,368,737 A | 1/1983 | Ash |
| 4,375,346 A | 3/1983 | Kraus et al. |
| 4,381,003 A | 4/1983 | Buoncristiani |
| 4,381,005 A | 4/1983 | Bujan |
| 4,382,753 A | 5/1983 | Archibald |
| 4,387,184 A | 6/1983 | Coquard et al. |
| 4,391,600 A | 7/1983 | Archibald |
| 4,396,382 A | 8/1983 | Goldhaber |
| 4,398,910 A | 8/1983 | Blake et al. |
| 4,405,667 A | 9/1983 | Christensen et al. |
| 4,405,774 A | 9/1983 | Miwa et al. |
| 4,407,877 A | 10/1983 | Rasmussen |
| 4,407,888 A | 10/1983 | Crofts |
| 4,410,164 A | 10/1983 | Kamen |
| 4,410,322 A | 10/1983 | Archibald |
| 4,411,649 A | 10/1983 | Kamen |
| 4,412,917 A | 11/1983 | Ahjopalo |
| 4,417,753 A | 11/1983 | Bacehowski |
| 4,429,076 A | 1/1984 | Saito et al. |
| D272,651 S | 2/1984 | Mahurkar |
| 4,430,048 A | 2/1984 | Fritsch |
| 4,438,238 A | 3/1984 | Fukushima et al. |
| 4,449,976 A | 5/1984 | Kamen |
| 4,456,218 A | 6/1984 | Kawabata et al. |
| 4,464,172 A | 8/1984 | Lichtenstein |
| 4,465,481 A | 8/1984 | Blake |
| 4,468,222 A | 8/1984 | Lundquist |
| 4,472,116 A | 9/1984 | Wenstrup |
| 4,472,117 A | 9/1984 | Wenstrup |
| 4,473,342 A | 9/1984 | Iles |
| 4,479,760 A | 10/1984 | Bilstad et al. |
| 4,479,761 A | 10/1984 | Bilstad et al. |
| 4,479,762 A | 10/1984 | Bilstad et al. |
| 4,479,989 A | 10/1984 | Mahal |
| 4,490,137 A | 12/1984 | Moukheibir |
| 4,496,349 A | 1/1985 | Cosentino |
| 4,498,902 A | 2/1985 | Ash et al. |
| 4,504,038 A | 3/1985 | King |
| 4,521,437 A | 6/1985 | Storms |
| 4,530,759 A | 7/1985 | Schal |
| 4,537,561 A | 8/1985 | Xanthopoulos |
| 4,543,087 A | 9/1985 | Sommercorn et al. |
| 4,547,136 A | 10/1985 | Rothstein |
| 4,548,348 A | 10/1985 | Clements |
| 4,552,552 A | 11/1985 | Polaschegg et al. |
| 4,559,036 A | 12/1985 | Wunsch |
| 4,559,044 A | 12/1985 | Robinson et al. |
| 4,560,472 A | 12/1985 | Granzow et al. |
| 4,562,118 A | 12/1985 | Maruhashi et al. |
| 4,568,723 A | 2/1986 | Lu |
| 4,573,994 A | 3/1986 | Fischell et al. |
| 4,574,173 A | 3/1986 | Bennett |
| 4,581,012 A | 4/1986 | Brown et al. |
| 4,585,436 A | 4/1986 | Davis et al. |
| 4,586,920 A | 5/1986 | Peabody |
| 4,588,648 A | 5/1986 | Krueger |
| 4,599,055 A | 7/1986 | Dykstra |
| 4,599,276 A | 7/1986 | Martini |
| 4,600,401 A | 7/1986 | Kamen |
| 4,613,327 A | 9/1986 | Tegrarian et al. |
| 4,618,343 A | 10/1986 | Polaschegg |
| 4,620,690 A | 11/1986 | Kamen |
| RE32,303 E | 12/1986 | Lasker et al. |
| 4,627,844 A | 12/1986 | Schmitt |
| 4,628,969 A | 12/1986 | Jurgens, Jr. et al. |
| 4,634,426 A | 1/1987 | Kamen |
| 4,634,430 A | 1/1987 | Polaschegg |
| 4,636,412 A | 1/1987 | Field |
| 4,639,245 A | 1/1987 | Pastrone et al. |
| 4,640,870 A | 2/1987 | Akazawa et al. |
| 4,642,098 A | 2/1987 | Lundquist |
| 4,643,926 A | 2/1987 | Mueller |
| 4,648,810 A | 3/1987 | Schippers et al. |
| 4,648,872 A | 3/1987 | Kamen |
| 4,657,490 A | 4/1987 | Abbott |
| 4,668,752 A | 5/1987 | Tominari et al. |
| 4,673,334 A | 6/1987 | Allington et al. |
| 4,681,564 A | 7/1987 | Landreneau |
| 4,681,797 A | 7/1987 | Van Iseghem |
| 4,686,125 A | 8/1987 | Johnston et al. |
| 4,687,471 A | 8/1987 | Twardowski et al. |
| 4,692,361 A | 9/1987 | Johnston et al. |
| 4,694,848 A | 9/1987 | Jorgensen et al. |
| 4,696,671 A | 9/1987 | Epstein et al. |
| 4,703,773 A | 11/1987 | Hansen et al. |
| 4,704,102 A | 11/1987 | Guthery |
| 4,707,389 A | 11/1987 | Ward |
| 4,717,117 A | 1/1988 | Cook |
| 4,718,890 A * | 1/1988 | Peabody .................. 604/29 |

| | | | | | |
|---|---|---|---|---|---|
| 4,724,028 A | 2/1988 | Zabielski et al. | 4,976,162 A | 12/1990 | Kamen |
| 4,726,997 A | 2/1988 | Mueller et al. | 4,977,213 A | 12/1990 | Giroud-Abel et al. |
| 4,732,795 A | 3/1988 | Ohya et al. | 4,990,054 A | 2/1991 | Janocko |
| 4,734,327 A | 3/1988 | Vicik | 4,992,511 A | 2/1991 | Yamamoto et al. |
| 4,735,558 A | 4/1988 | Kienholz et al. | 4,996,054 A | 2/1991 | Pietsch et al. |
| 4,735,855 A | 4/1988 | Wofford et al. | 4,999,254 A | 3/1991 | Ofstein |
| 4,740,582 A | 4/1988 | Coquard et al. | 5,002,471 A | 3/1991 | Perlov |
| 4,747,822 A | 5/1988 | Peabody | 5,003,019 A | 3/1991 | Ishimaru et al. |
| 4,749,109 A | 6/1988 | Kamen | 5,004,459 A | 4/1991 | Peabody et al. |
| 4,753,222 A | 6/1988 | Morishita | 5,006,050 A | 4/1991 | Cooke et al. |
| 4,760,114 A | 7/1988 | Haaf et al. | 5,006,601 A | 4/1991 | Lutz et al. |
| 4,762,864 A | 8/1988 | Goel et al. | 5,008,204 A | 4/1991 | Stehling |
| 4,764,404 A | 8/1988 | Genske et al. | 5,008,356 A | 4/1991 | Ishimaru et al. |
| 4,767,377 A | 8/1988 | Falla | 5,017,652 A | 5/1991 | Abe et al. |
| 4,767,651 A | 8/1988 | Starczewski et al. | 5,019,140 A | 5/1991 | Bowser et al. |
| 4,769,134 A | 9/1988 | Allan et al. | 5,034,457 A | 7/1991 | Serini et al. |
| 4,772,269 A | 9/1988 | Twardowski et al. | 5,034,458 A | 7/1991 | Serini et al. |
| 4,772,497 A | 9/1988 | Maasola | 5,037,385 A | 8/1991 | O'Byrne |
| 4,778,356 A | 10/1988 | Hicks | 5,043,088 A | 8/1991 | Falla |
| 4,778,450 A | 10/1988 | Kamen | 5,044,902 A | 9/1991 | Malbec |
| 4,778,451 A | 10/1988 | Kamen | 5,053,023 A | 10/1991 | Martin |
| 4,778,697 A | 10/1988 | Genske et al. | 5,053,457 A | 10/1991 | Lee |
| 4,784,576 A | 11/1988 | Bloom et al. | 5,057,073 A | 10/1991 | Martin |
| 4,786,697 A | 11/1988 | Cozewith et al. | 5,057,075 A | 10/1991 | Moncrief et al. |
| 4,789,714 A | 12/1988 | Cozewith et al. | 5,062,774 A | 11/1991 | Kramer et al. |
| 4,792,488 A | 12/1988 | Schirmer | 5,071,686 A | 12/1991 | Genske et al. |
| 4,794,942 A | 1/1989 | Yasuda et al. | 5,071,911 A | 12/1991 | Furuta et al. |
| 4,795,782 A | 1/1989 | Lutz et al. | 5,071,912 A | 12/1991 | Furuta et al. |
| 4,798,580 A | 1/1989 | DeMeo et al. | 5,075,376 A | 12/1991 | Furuta et al. |
| 4,800,129 A | 1/1989 | Deak | 5,079,295 A | 1/1992 | Furuta et al. |
| 4,803,102 A | 2/1989 | Raniere et al. | 5,085,649 A | 2/1992 | Flynn |
| 4,808,161 A | 2/1989 | Kamen | 5,087,677 A | 2/1992 | Brekner et al. |
| 4,816,019 A | 3/1989 | Kamen | 5,088,515 A | 2/1992 | Kamen |
| 4,816,343 A | 3/1989 | Mueller | 5,093,164 A | 3/1992 | Bauer et al. |
| 4,818,186 A | 4/1989 | Pastrone et al. | 5,093,194 A | 3/1992 | Touhsaent et al. |
| 4,818,190 A | 4/1989 | Pelmulder et al. | 5,094,820 A | 3/1992 | Maxwell et al. |
| 4,823,552 A | 4/1989 | Ezell et al. | 5,094,921 A | 3/1992 | Itamura et al. |
| 4,824,339 A | 4/1989 | Bainbridge et al. | 5,098,262 A | 3/1992 | Wecker et al. |
| 4,826,482 A | 5/1989 | Kamen | 5,098,413 A | 3/1992 | Trudell et al. |
| 4,828,545 A | 5/1989 | Epstein et al. | 5,106,366 A | 4/1992 | Steppe |
| 4,830,586 A | 5/1989 | Herter et al. | 5,106,368 A | 4/1992 | Uldall et al. |
| 4,832,054 A | 5/1989 | Bark | 5,108,844 A | 4/1992 | Blemberg et al. |
| 4,834,755 A | 5/1989 | Silvestrini et al. | 5,110,642 A | 5/1992 | Genske et al. |
| 4,842,582 A | 6/1989 | Mahurkar | 5,116,906 A | 5/1992 | Mizuno et al. |
| 4,842,584 A | 6/1989 | Pastrone | 5,120,303 A | 6/1992 | Hombrouckx |
| 4,842,948 A | 6/1989 | Gagliani et al. | 5,125,891 A | 6/1992 | Hossain et al. |
| 4,848,722 A | 7/1989 | Webster | 5,129,894 A | 7/1992 | Sommermeyer et al. |
| 4,850,805 A | 7/1989 | Madsen et al. | 5,132,363 A | 7/1992 | Furuta et al. |
| 4,852,851 A | 8/1989 | Webster | 5,133,650 A | 7/1992 | Sunderland et al. |
| 4,855,356 A | 8/1989 | Holub et al. | 5,135,485 A | 8/1992 | Cohen et al. |
| 4,856,259 A | 8/1989 | Woo et al. | 5,135,785 A | 8/1992 | Millon |
| 4,856,260 A | 8/1989 | Woo et al. | 5,141,493 A | 8/1992 | Jacobsen et al. |
| 4,859,319 A | 8/1989 | Borsari | 5,145,731 A | 9/1992 | Lund et al. |
| 4,861,242 A | 8/1989 | Finsterwald | 5,154,979 A | 10/1992 | Kerschbaumer et al. |
| 4,863,996 A | 9/1989 | Nakazima et al. | 5,159,004 A | 10/1992 | Furuta et al. |
| 4,865,584 A | 9/1989 | Epstein et al. | 5,163,900 A | 11/1992 | Wortrich |
| 4,871,799 A | 10/1989 | Kobayashi et al. | 5,164,267 A | 11/1992 | D'Heur et al. |
| 4,872,813 A | 10/1989 | Gorton et al. | 5,176,634 A | 1/1993 | Smith et al. |
| 4,873,287 A | 10/1989 | Holub et al. | 5,176,956 A | 1/1993 | Jevne et al. |
| 4,877,682 A | 10/1989 | Sauers et al. | 5,176,959 A | 1/1993 | Yamada et al. |
| 4,885,119 A | 12/1989 | Mueller et al. | 5,178,182 A | 1/1993 | Kamen |
| 4,886,431 A | 12/1989 | Soderquist et al. | 5,183,706 A | 2/1993 | Bekele |
| 4,886,432 A | 12/1989 | Kimberlin | 5,185,084 A | 2/1993 | Lapidus et al. |
| 4,895,561 A | 1/1990 | Mahurkar | 5,185,189 A | 2/1993 | Stenger et al. |
| 4,904,168 A | 2/1990 | Cavoto et al. | 5,188,593 A | 2/1993 | Martin |
| 4,910,085 A | 3/1990 | Raniere et al. | 5,189,091 A | 2/1993 | Laughner |
| 4,923,470 A | 5/1990 | Dumican | 5,193,913 A | 3/1993 | Rosenbaum |
| 4,927,411 A | 5/1990 | Pastrone et al. | 5,193,990 A | 3/1993 | Kamen et al. |
| 4,929,479 A | 5/1990 | Shishido et al. | 5,194,316 A | 3/1993 | Horner et al. |
| 4,931,520 A | 6/1990 | Yamanashi et al. | 5,195,960 A | 3/1993 | Hossain et al. |
| 4,935,004 A | 6/1990 | Cruz | 5,195,986 A | 3/1993 | Kamen |
| 4,937,299 A | 6/1990 | Ewen et al. | 5,196,254 A | 3/1993 | Akiyama |
| 4,941,519 A | 7/1990 | Sestak et al. | 5,197,951 A | 3/1993 | Mahurkar |
| 4,942,735 A | 7/1990 | Mushika et al. | 5,203,943 A | 4/1993 | Nornberg et al. |
| 4,946,616 A | 8/1990 | Falla et al. | 5,206,290 A | 4/1993 | Mizuno et al. |
| 4,950,720 A | 8/1990 | Randall, Jr. et al. | 5,207,642 A | 5/1993 | Orkin et al. |
| 4,957,966 A | 9/1990 | Nishio et al. | 5,207,650 A | 5/1993 | Martin |
| 4,957,967 A | 9/1990 | Mizuno et al. | 5,207,983 A | 5/1993 | Liebert et al. |
| 4,966,795 A | 10/1990 | Genske et al. | 5,209,723 A | 5/1993 | Twardowski et al. |

| | | | | | |
|---|---|---|---|---|---|
| 5,211,201 A | 5/1993 | Kamen et al. | 5,423,768 A | 6/1995 | Folden et al. |
| 5,212,238 A | 5/1993 | Scheibelhoffer et al. | 5,427,509 A | 6/1995 | Chapman et al. |
| 5,213,483 A | 5/1993 | Flaherty et al. | 5,429,485 A | 7/1995 | Dodge |
| 5,215,312 A | 6/1993 | Knappe et al. | 5,431,626 A | 7/1995 | Bryant et al. |
| 5,215,450 A | 6/1993 | Tamari | 5,433,588 A | 7/1995 | Monk et al. |
| 5,218,048 A | 6/1993 | Abe et al. | 5,438,510 A | 8/1995 | Bryant et al. |
| 5,218,049 A | 6/1993 | Yamamoto et al. | 5,439,587 A | 8/1995 | Stankowski et al. |
| 5,221,255 A | 6/1993 | Mahurkar et al. | 5,442,919 A | 8/1995 | Wilhelm |
| 5,221,256 A | 6/1993 | Mahurkar | 5,445,506 A | 8/1995 | Afflerbaugh et al. |
| 5,222,946 A | 6/1993 | Kamen | 5,446,270 A | 8/1995 | Chamberlain et al. |
| 5,230,614 A | 7/1993 | Zanger et al. | 5,457,249 A | 10/1995 | Sagane et al. |
| 5,230,934 A | 7/1993 | Sakano et al. | 5,458,468 A | 10/1995 | Ye et al. |
| 5,230,935 A | 7/1993 | Delimoy et al. | 5,460,490 A | 10/1995 | Carr et al. |
| 5,238,997 A | 8/1993 | Bauer et al. | 5,460,493 A | 10/1995 | Deniega et al. |
| 5,241,985 A | 9/1993 | Faust et al. | 5,462,416 A | 10/1995 | Dennehey et al. |
| 5,244,971 A | 9/1993 | Jean-Marc | 5,464,388 A | 11/1995 | Merte et al. |
| 5,245,151 A | 9/1993 | Chamberlain et al. | 5,464,398 A | 11/1995 | Haindl |
| 5,245,693 A | 9/1993 | Ford et al. | 5,474,683 A | 12/1995 | Bryant et al. |
| 5,247,434 A | 9/1993 | Peterson et al. | 5,475,060 A | 12/1995 | Brekner et al. |
| 5,250,027 A | 10/1993 | Lewis et al. | 5,476,368 A | 12/1995 | Rabenau et al. |
| 5,250,041 A | 10/1993 | Folden et al. | 5,480,294 A | 1/1996 | Di Perna et al. |
| 5,252,044 A | 10/1993 | Raines et al. | 5,482,440 A | 1/1996 | Dennehey et al. |
| 5,254,084 A | 10/1993 | Geary | 5,482,770 A | 1/1996 | Bekele |
| 5,254,824 A | 10/1993 | Chamberlain et al. | 5,487,649 A | 1/1996 | Dorsey, III et al. |
| 5,257,917 A | 11/1993 | Minarik et al. | 5,498,338 A | 3/1996 | Kruger et al. |
| 5,258,230 A | 11/1993 | LaFleur et al. | 5,498,677 A | 3/1996 | Weller |
| 5,272,235 A | 12/1993 | Wakatsuru et al. | 5,508,051 A | 4/1996 | Falla et al. |
| 5,277,820 A | 1/1994 | Ash | 5,514,102 A | 5/1996 | Winterer et al. |
| 5,278,231 A | 1/1994 | Chundury | 5,518,378 A | 5/1996 | Neftel et al. |
| 5,278,377 A | 1/1994 | Tsai | 5,522,769 A | 6/1996 | DeGuiseppi |
| 5,288,531 A | 2/1994 | Falla et al. | 5,525,659 A | 6/1996 | Falla et al. |
| 5,288,560 A | 2/1994 | Sudo et al. | 5,526,844 A | 6/1996 | Kamen |
| 5,288,799 A | 2/1994 | Schmid et al. | 5,527,274 A | 6/1996 | Zakko |
| 5,290,856 A | 3/1994 | Okamoto | 5,529,708 A | 6/1996 | Palmgren et al. |
| 5,292,306 A | 3/1994 | Wynkoop et al. | 5,530,065 A | 6/1996 | Farley et al. |
| 5,294,763 A | 3/1994 | Chamberlain et al. | 5,533,389 A | 7/1996 | Kamen et al. |
| 5,302,093 A | 4/1994 | Owens et al. | 5,534,606 A | 7/1996 | Bennett et al. |
| 5,306,542 A | 4/1994 | Bayer | 5,536,412 A | 7/1996 | Ash |
| 5,312,867 A | 5/1994 | Mitsuno et al. | 5,540,808 A | 7/1996 | Vincent et al. |
| 5,316,452 A | 5/1994 | Bogen et al. | 5,542,919 A | 8/1996 | Simon et al. |
| 5,317,059 A | 5/1994 | Chundury et al. | 5,552,504 A | 9/1996 | Bennett et al. |
| 5,322,519 A | 6/1994 | Ash | 5,554,013 A | 9/1996 | Owens et al. |
| 5,331,057 A | 7/1994 | Brekner et al. | 5,556,263 A | 9/1996 | Jacobsen et al. |
| 5,332,372 A | 7/1994 | Reynolds | 5,569,026 A | 10/1996 | Novak |
| 5,334,139 A | 8/1994 | Jeppsson et al. | 5,569,182 A | 10/1996 | Twardowski et al. |
| 5,336,173 A | 8/1994 | Folden | 5,570,716 A | 11/1996 | Kamen et al. |
| 5,336,190 A | 8/1994 | Moss et al. | 5,575,310 A | 11/1996 | Kamen et al. |
| 5,338,293 A | 8/1994 | Jeppsson et al. | 5,575,632 A | 11/1996 | Morris et al. |
| 5,342,886 A | 8/1994 | Glotin et al. | 5,578,012 A | 11/1996 | Kamen et al. |
| 5,344,292 A | 9/1994 | Rabenau et al. | 5,580,460 A | 12/1996 | Polaschegg |
| 5,346,471 A | 9/1994 | Raulerson | 5,580,914 A | 12/1996 | Falla et al. |
| 5,348,794 A | 9/1994 | Takahashi | 5,583,192 A | 12/1996 | Bennett et al. |
| 5,350,357 A | 9/1994 | Kamen et al. | 5,586,868 A | 12/1996 | Lawless et al. |
| 5,350,358 A | 9/1994 | Martin | 5,588,815 A | 12/1996 | Zaleski, II |
| 5,356,676 A | 10/1994 | Von Widdern et al. | 5,588,816 A | 12/1996 | Abbott et al. |
| 5,359,001 A | 10/1994 | Epple et al. | 5,591,344 A * | 1/1997 | Kenley et al. ............... 210/636 |
| 5,360,648 A | 11/1994 | Falla et al. | 5,601,420 A | 2/1997 | Warner et al. |
| 5,364,344 A | 11/1994 | Beattie et al. | 5,603,354 A | 2/1997 | Jacobsen et al. |
| 5,364,371 A | 11/1994 | Kamen | 5,609,572 A | 3/1997 | Lang |
| 5,364,486 A | 11/1994 | Falla et al. | 5,610,253 A | 3/1997 | Hatke et al. |
| 5,371,151 A | 12/1994 | Berge et al. | 5,620,312 A | 4/1997 | Hyman et al. |
| 5,378,126 A | 1/1995 | Abrahamson et al. | 5,620,425 A | 4/1997 | Heffernan et al. |
| 5,378,230 A | 1/1995 | Mahurkar | 5,628,908 A | 5/1997 | Kamen et al. |
| 5,378,543 A | 1/1995 | Murata et al. | 5,629,398 A | 5/1997 | Okamoto et al. |
| 5,378,800 A | 1/1995 | Mok et al. | 5,630,935 A * | 5/1997 | Treu ............................ 210/130 |
| 5,380,276 A | 1/1995 | Miller et al. | 5,632,606 A | 5/1997 | Jacobsen et al. |
| 5,382,630 A | 1/1995 | Stehling et al. | 5,634,896 A | 6/1997 | Bryant et al. |
| 5,382,631 A | 1/1995 | Stehling et al. | 5,637,100 A | 6/1997 | Sudo |
| 5,385,540 A | 1/1995 | Abbott et al. | 5,637,400 A | 6/1997 | Brekner et al. |
| 5,387,645 A | 2/1995 | Montag et al. | 5,641,405 A | 6/1997 | Keshaviah et al. |
| 5,389,243 A | 2/1995 | Kaplan | 5,643,201 A | 7/1997 | Peabody et al. |
| 5,397,222 A | 3/1995 | Moss et al. | 5,645,734 A * | 7/1997 | Kenley et al. ............... 210/805 |
| 5,401,342 A | 3/1995 | Vincent et al. | 5,650,471 A | 7/1997 | Abe et al. |
| 5,409,355 A | 4/1995 | Brooke | 5,655,897 A | 8/1997 | Neftel et al. |
| 5,415,528 A | 5/1995 | Ogden et al. | 5,669,764 A | 9/1997 | Behringer et al. |
| 5,421,208 A | 6/1995 | Packard et al. | 5,674,944 A | 10/1997 | Falla et al. |
| 5,421,814 A | 6/1995 | Geary | 5,676,530 A | 10/1997 | Nazarifar |
| 5,421,823 A | 6/1995 | Kamen et al. | 5,685,867 A | 11/1997 | Twardowski et al. |
| 5,422,409 A | 6/1995 | Brekner et al. | 5,686,527 A | 11/1997 | Laurin et al. |

| | | | | | | |
|---|---|---|---|---|---|---|
| 5,693,728 | A | 12/1997 | Okamoto et al. | 6,059,544 A | 5/2000 | Jung et al. |
| 5,698,645 | A | 12/1997 | Weller et al. | 6,060,572 A | 5/2000 | Gillis et al. |
| 5,698,654 | A | 12/1997 | Nye et al. | 6,065,270 A | 5/2000 | Reinhard et al. |
| 5,707,751 | A | 1/1998 | Garza et al. | 6,065,941 A | 5/2000 | Gray et al. |
| 5,711,654 | A | 1/1998 | Afflerbaugh | 6,068,936 A | 5/2000 | Pfeiffer et al. |
| 5,718,569 | A | 2/1998 | Holst | 6,070,761 A | 6/2000 | Bloom et al. |
| 5,718,692 | A | 2/1998 | Schon et al. | 6,074,183 A | 6/2000 | Allen et al. |
| 5,721,025 | A | 2/1998 | Falla et al. | 6,074,359 A | 6/2000 | Keshaviah et al. |
| 5,722,947 | A | 3/1998 | Jeppsson et al. | 6,074,374 A | 6/2000 | Fulton |
| 5,723,189 | A | 3/1998 | Sudo | 6,077,246 A | 6/2000 | Kullas et al. |
| 5,733,991 | A | 3/1998 | Rohrmann et al. | 6,106,948 A | 8/2000 | Wang et al. |
| 5,741,125 | A | 4/1998 | Neftel et al. | 6,109,895 A | 8/2000 | Ray et al. |
| 5,744,664 | A | 4/1998 | Brekner et al. | 6,110,549 A | 8/2000 | Hamada et al. |
| 5,752,813 | A | 5/1998 | Tyner et al. | 6,110,617 A | 8/2000 | Feres |
| 5,756,623 | A | 5/1998 | Kreuder et al. | 6,114,457 A | 9/2000 | Markel et al. |
| 5,758,563 | A | 6/1998 | Robinson | 6,117,106 A | 9/2000 | Wasicek et al. |
| 5,776,111 | A | 7/1998 | Tesio | 6,117,465 A | 9/2000 | Falla et al. |
| 5,782,575 | A | 7/1998 | Vincent et al. | 6,121,394 A | 9/2000 | Sugimoto et al. |
| 5,788,670 | A | 8/1998 | Reinhard et al. | 6,126,403 A | 10/2000 | Yamada |
| 5,788,671 | A | 8/1998 | Johnson | 6,126,631 A | 10/2000 | Loggie |
| 5,788,680 | A | 8/1998 | Linder | 6,129,699 A | 10/2000 | Haight et al. |
| 5,790,752 | A | 8/1998 | Anglin et al. | 6,132,405 A | 10/2000 | Nilsson et al. |
| 5,792,824 | A | 8/1998 | Natori | 6,136,744 A | 10/2000 | Gillis et al. |
| 5,795,326 | A | 8/1998 | Simán | 6,146,354 A | 11/2000 | Beil |
| 5,795,945 | A | 8/1998 | Natori | 6,147,025 A | 11/2000 | Gillis et al. |
| 5,807,075 | A | 9/1998 | Jacobsen et al. | 6,156,016 A | 12/2000 | Maginot |
| 5,807,311 | A | 9/1998 | Palestrant | 6,159,195 A | 12/2000 | Ha et al. |
| 5,814,004 | A | 9/1998 | Tamari | 6,165,154 A | 12/2000 | Gray et al. |
| 5,816,779 | A | 10/1998 | Lawless et al. | 6,168,862 B1 | 1/2001 | Rosenbaum et al. |
| 5,836,908 | A | 11/1998 | Beden et al. | 6,169,052 B1 | 1/2001 | Brekner et al. |
| 5,849,843 | A | 12/1998 | Laurin et al. | 6,171,670 B1 | 1/2001 | Sudo et al. |
| 5,854,347 | A | 12/1998 | Laurin et al. | 6,186,752 B1 | 2/2001 | Deniega et al. |
| 5,854,349 | A | 12/1998 | Abe et al. | 6,190,349 B1 | 2/2001 | Ash et al. |
| 5,863,986 | A | 1/1999 | Herrmann-Schonherr et al. | 6,190,371 B1 | 2/2001 | Maginot et al. |
| 5,871,566 | A | 2/1999 | Rutz | 6,191,254 B1 | 2/2001 | Falla et al. |
| 5,872,201 | A | 2/1999 | Cheung et al. | 6,193,684 B1 | 2/2001 | Burbank et al. |
| 5,879,768 | A | 3/1999 | Falla et al. | 6,203,296 B1 | 3/2001 | Ray et al. |
| 5,899,674 | A | 5/1999 | Jung et al. | 6,206,849 B1 | 3/2001 | Martin et al. |
| 5,906,598 | A | 5/1999 | Giesler et al. | 6,208,107 B1 | 3/2001 | Maske et al. |
| 5,919,369 | A | 7/1999 | Ash | 6,210,361 B1 | 4/2001 | Kamen et al. |
| 5,921,951 | A | 7/1999 | Morris | 6,221,648 B1 | 4/2001 | Le Page et al. |
| 5,924,975 | A | 7/1999 | Goldowsky | 6,223,130 B1 | 4/2001 | Gray et al. |
| 5,927,956 | A | 7/1999 | Lim et al. | 6,225,426 B1 | 5/2001 | Gillis et al. |
| 5,928,196 | A | 7/1999 | Johnson et al. | 6,225,427 B1 | 5/2001 | Burton et al. |
| 5,931,647 | A | 8/1999 | Jacobsen et al. | 6,228,047 B1 * | 5/2001 | Dadson .................... 604/29 |
| 5,931,808 | A | 8/1999 | Pike | 6,231,320 B1 | 5/2001 | Lawless et al. |
| 5,931,829 | A | 8/1999 | Burbank et al. | 6,234,991 B1 | 5/2001 | Gorsuch |
| 5,938,634 | A | 8/1999 | Packard | 6,234,997 B1 | 5/2001 | Kamen et al. |
| 5,942,579 | A | 8/1999 | Falla et al. | RE37,208 E | 6/2001 | Winter et al. |
| 5,944,495 | A | 8/1999 | Jacobsen et al. | 6,245,039 B1 | 6/2001 | Brugger et al. |
| 5,944,684 | A | 8/1999 | Roberts et al. | 6,248,092 B1 | 6/2001 | Miraki et al. |
| 5,947,953 | A | 9/1999 | Ash et al. | 6,248,093 B1 | 6/2001 | Moberg |
| 5,961,486 | A | 10/1999 | Twardowski et al. | 6,254,567 B1 | 7/2001 | Treu et al. |
| 5,964,796 | A | 10/1999 | Imran | 6,255,396 B1 | 7/2001 | Ding et al. |
| 5,965,433 | A | 10/1999 | Gardetto et al. | 6,258,079 B1 | 7/2001 | Burbank et al. |
| 5,968,009 | A | 10/1999 | Simán | 6,261,655 B1 | 7/2001 | Rosenbaum et al. |
| 5,976,103 | A | 11/1999 | Martin | 6,266,664 B1 | 7/2001 | Russell-Falla et al. |
| 5,980,495 | A | 11/1999 | Heinz et al. | 6,270,673 B1 | 8/2001 | Belt et al. |
| 5,983,136 | A | 11/1999 | Kamen | 6,280,408 B1 | 8/2001 | Sipin |
| 5,984,762 | A | 11/1999 | Tedeschi et al. | 6,280,423 B1 | 8/2001 | Davey et al. |
| 5,989,206 | A | 11/1999 | Prosl et al. | 6,290,669 B1 | 9/2001 | Zicherman |
| 5,989,423 | A | 11/1999 | Kamen et al. | 6,293,926 B1 | 9/2001 | Sorensen et al. |
| 5,990,254 | A | 11/1999 | Weller et al. | 6,302,653 B1 | 10/2001 | Bryant et al. |
| 5,993,949 | A | 11/1999 | Rosenbaum et al. | 6,302,875 B1 | 10/2001 | Makower et al. |
| 5,998,019 | A | 12/1999 | Rosenbaum et al. | 6,343,614 B1 | 2/2002 | Gray et al. |
| 6,001,078 | A | 12/1999 | Reekers | 6,364,857 B1 | 4/2002 | Gray et al. |
| 6,001,079 | A | 12/1999 | Pourchez | 6,372,848 B1 | 4/2002 | Yang et al. |
| 6,001,201 | A | 12/1999 | Vincent et al. | 6,382,923 B1 | 5/2002 | Gray |
| 6,007,310 | A | 12/1999 | Jacobsen et al. | 6,409,699 B1 | 6/2002 | Ash |
| 6,007,520 | A | 12/1999 | Sudo | 6,416,293 B1 | 7/2002 | Bouchard |
| 6,017,194 | A | 1/2000 | North, Jr. | 6,491,656 B1 * | 12/2002 | Morris .................... 604/6.09 |
| 6,020,444 | A | 2/2000 | Riedel et al. | 6,491,658 B1 | 12/2002 | Miura et al. |
| 6,030,359 | A * | 2/2000 | Nowosielski ............... 604/65 | 6,497,676 B1 | 12/2002 | Childers et al. |
| 6,036,458 | A | 3/2000 | Cole et al. | 6,503,062 B1 | 1/2003 | Gray et al. |
| 6,036,668 | A | 3/2000 | Mathis | 6,558,340 B1 | 5/2003 | Traeger |
| 6,041,801 | A | 3/2000 | Gray et al. | 6,561,996 B1 | 5/2003 | Gorsuch |
| 6,045,648 | A | 4/2000 | Palmgren et al. | 6,561,997 B1 | 5/2003 | Weitzel et al. |
| 6,048,329 | A | 4/2000 | Thompson et al. | 6,585,682 B1 | 7/2003 | Haraldsson et al. |
| 6,056,522 | A | 5/2000 | Johnson | 6,592,542 B2 | 7/2003 | Childers et al. |

| | | |
|---|---|---|
| 6,595,948 B2 | 7/2003 | Suzuki et al. |
| 6,666,842 B1 | 12/2003 | Sakai |
| 6,743,201 B1 | 6/2004 | Dönig et al. |
| 6,808,369 B2 | 10/2004 | Gray et al. |
| 6,814,547 B2 | 11/2004 | Childers et al. |
| 6,869,538 B2 | 3/2005 | Yu et al. |
| 6,949,079 B1 | 9/2005 | Westberg et al. |
| 7,004,924 B1 | 2/2006 | Brugger et al. |
| 2001/0014793 A1 | 8/2001 | Brugger et al. |
| 2001/0018937 A1 | 9/2001 | Nemoto |
| 2002/0045851 A1 | 4/2002 | Suzuki et al. |
| 2002/0077598 A1 | 6/2002 | Yap et al. |
| 2003/0012905 A1 | 1/2003 | Zumbrum et al. |
| 2003/0195454 A1 | 10/2003 | Wariar et al. |
| 2003/0204162 A1 | 10/2003 | Childers et al. |
| 2003/0220600 A1 | 11/2003 | Gotch et al. |
| 2004/0254513 A1 | 12/2004 | Shang et al. |
| 2005/0118038 A1 | 6/2005 | Gray et al. |

FOREIGN PATENT DOCUMENTS

| | | |
|---|---|---|
| DE | 133 411 Z | 1/1979 |
| DE | 3522782 A1 | 1/1987 |
| DE | 251 904 A3 | 12/1987 |
| DE | 3739556 A1 | 6/1989 |
| DE | 39 37 865 A1 | 6/1990 |
| EP | 0028371 | 5/1981 |
| EP | 0 033 096 | 8/1981 |
| EP | 0 052 004 | 5/1982 |
| EP | 0 097 432 | 1/1984 |
| EP | 0 156 464 A1 | 10/1985 |
| EP | 0 157 024 | 10/1985 |
| EP | 0 206 195 | 12/1986 |
| EP | 0204260 | 12/1986 |
| EP | 0 306 664 A2 | 3/1989 |
| EP | 0319272 | 6/1989 |
| EP | 0 333 308 B1 | 9/1989 |
| EP | 0 381 042 A1 | 8/1990 |
| EP | 0402505 | 12/1990 |
| EP | 0011935 | 5/1991 |
| EP | 0 216 509 B1 | 9/1991 |
| EP | 0248632 | 4/1992 |
| EP | 0 497 567 A2 | 8/1992 |
| EP | 0 504 934 B1 | 9/1992 |
| EP | 0 524 802 A1 | 1/1993 |
| EP | 0 535 874 B1 | 4/1993 |
| EP | 0 554 722 A1 | 8/1993 |
| EP | 0 283 164 B1 | 5/1995 |
| EP | 0 660 725 | 7/1995 |
| EP | 0 492 982 B1 | 8/1995 |
| EP | 0 684 845 B1 | 12/1995 |
| EP | 0 430 585 B1 | 1/1996 |
| EP | 0 156 464 B1 | 5/1996 |
| EP | 0 582 355 B1 | 5/1996 |
| EP | 0 709 105 A1 | 5/1996 |
| EP | 0 203 799 B1 | 8/1996 |
| EP | 0 384 694 B1 | 9/1996 |
| EP | 0 497 567 B1 | 9/1996 |
| EP | 0 291 208 B1 | 8/1997 |
| EP | 0 790 063 A1 | 8/1997 |
| EP | 0 291 208 A2 | 11/1998 |
| EP | 0 680 401 B1 | 1/1999 |
| EP | 1 110 564 A2 | 6/2001 |
| EP | 1 110 565 A2 | 6/2001 |
| EP | 0 709 105 131 | 12/2001 |
| FR | 2371931 | 6/1978 |
| FR | 2440740 | 6/1980 |
| GB | 1326236 | 8/1973 |
| GB | 2245 496 A | 1/1992 |
| JP | 03-095286 | 4/1991 |
| JP | 05-277154 | 10/1993 |
| JP | 11-071554 | 3/1999 |
| SE | 331736 | 1/1971 |
| WO | WO 84/02473 | 7/1984 |
| WO | WO 85/04813 | 11/1985 |
| WO | WO 86/01115 | 2/1986 |
| WO | 87/05223 | 9/1987 |
| WO | WO 88/03389 | 5/1988 |
| WO | 89/01795 | 3/1989 |
| WO | 90/13795 | 11/1990 |
| WO | WO 91/02484 | 3/1991 |
| WO | WO 92/15349 | 9/1992 |
| WO | WO 93/01845 | 2/1993 |
| WO | 94/20158 | 9/1994 |
| WO | WO 95/35124 | 12/1995 |
| WO | WO 97/08054 | 3/1997 |
| WO | WO 98/17333 | 4/1998 |
| WO | WO 98/27926 | 7/1998 |
| WO | WO 98/44043 | 10/1998 |
| WO | WO 98/50088 | 11/1998 |
| WO | WO 99/06082 | 2/1999 |
| WO | WO 99/07301 | 2/1999 |
| WO | WO 99/48990 | 9/1999 |
| WO | WO 99/06082 | 11/1999 |
| WO | WO 00/10385 | 3/2000 |
| WO | WO 00/20050 | 4/2000 |
| WO | WO 01/58509 A1 | 8/2001 |
| WO | WO 01/91829 | 12/2001 |

OTHER PUBLICATIONS

Durand, P. et al. Measurement of Hydrostatic Intraperitoneal Pressure: A Necessary Routine Test in Peritoneal Dialysis; *Peritonial Dialysis International*, vol. 16, 1996, pp. S84-S87.

Durand, P. et al., *Routine Measurement of Hydrostatic Intraperitoneal Pressure*, Advances in Peritoneal Dialysis, pp. 108-112.

Gotloib, L. et al., *Hemodynamic Effects of Increasing Intra-Abdominal Pressure in Peritoneal Dialysis*, pp. 41-43.

Mathieu et al., Measurement of Hydrostatic Intraperitoneal Pressure, *Advances in Peritoneal Dialysis*, vol. 10, 1994, pp. 59-62.

Twardowski, Z. et al., High Volume, Low Frequency Continuous Ambulatory Peritoneal Dialysis, *Kidney International*, Vo. 23, 1983, pp. 64-70.

Fresinius Medical Care, *The Sign for Safe and Bicompatible CAPD, Stay Safe® Balance*, 8 pages.

Help Cards entitles "HomeChoice, Augomated PD System", from Baxter Healthcare Corporation, 1994.

Help Cards entitled "PAC-Xtra Help Cards", from Baxter Healthcare Corporation, 1991.

Booklet entitled "HomeChoice, Patient At-Home Guide, HomeChoice Automated PD System", from Baxter Healthcare Corporation, 1994.

Brochure entitled "Pac-Xtra, Peritoneal Automated Cycler with X-Connector Set", from Baxter Healthcare Corporation, 1990.

Brochure entitled "PD Today, Understanding Home Training Fees: A Physician Perspective", from Baxter Healthcare Corporation, 1999.

Booklet entitled "HomeChoice Automated PD System, Advanced Technology Creates a New Way to Go Home", from Baxter Healthcare Corporation, 1994.

Booklet entitled "Issues and Strategies in Peritoneal Dialysis: Toward Prescription Dialysis, Highlights of a Clinical Conference", Part One, from Medical Education Programs, Ltd. under a grant from Baxter Healthcare Corporation.

Intraperitoneal Pressure, Presentation by Jane Hollis, et al., Addenbrooke's Dialysis Center, UK, 1998.

"We Have a Gripe With Equal Treatment," Brochure published by Baxter Healthcare Corporation (1988).

Defendants' Preliminary Invalidity Contentions for U.S. Patent No. 5,421,823 Aug. 24, 2007.

Appendix A: U.S. Patent No. 3,620,215 Alone and in Combination with Other Prior Art References.

Appendix B: Pericycle Product and References Describing the Pericycle in Combination with Other Prior Art References.

Appendix C: U.S. Patent No. 4,412,917 in Combination with Other Prior Art References.

Appendix D: U.S. Patent No. 4,498,900 in Combination with Other Prior Art References.

Appendix E: U.S. Patent No. 3,545,438 in Combination with Other Prior Art References.

Appendix F: U.S. patent No. 5,004,459 in Combination with Other Prior Art References.

Appendix G: Bilstad and Kruger References Together or in Combination with Other Prior Art References.

Appendix H: Combination of 90/2 and Bilstad Together, or in Combination with Other References.
Appendix I: French Patent Nos. 2,371,931 and 2,240,740 in Combination with Other Prior Art References.
Appendix J: AP Hauni References in Combination with Other Prior Art References.
Appendix K: the SIF 901 References in Combination with Other Prior Art References.
Appendix L: "PD in the 90s" in Combination with Other Prior Art References.
Opening Expert Witness Report of Dr. Juan Santiago Regarding Anticipation and Obviousness of the Claims of U.S. Patents Nos. 6,503,062 and 6,808,369 in view of the Prior Art and based on the Indefiniteness, Lack of Enablement, and Lack of Written Description of Certain Claims of U.S. Patent Nos. 6,503,062 and 6,808,369, Apr. 24, 2009.
Opening Expert. Witness Report of William K. Durfee Regarding whether Certain Claims of U.S. Patent No. 5,324,422, U.S. Patent No. 5,421,823, U.S. Patent No. 5,431,626 and U.S. Patent No. 5,438,510 were Ready for Patenting, Apr. 24, 2009.
Expert Witness Report of Fred K. Forster: Analysis of Obviousness of Certain Asserted Claims of U.S. Patent Nos. 5,431,626; 5,324,422; and 5,438,510, Apr. 24,,2009.
Expert Witness Report of Ronald J. Adrian Regarding Lack of Written Description, Lack of Enablement, and Indefiniteness of the Asserted Claim (Claim 12) of U.S. Patent No. 6,814,547, Apr. 24, 2009.
Exhibit A, Credentials of Ronald J. Adrian.
Exhibit B, Materials Considered by Ronald J. Adrian.
Expert Report on Development of the PD700 and Motivation to Combine the PD700 and U.S. Patent No. 5,088,515, Sven Olofsson, Apr. 24, 2009.
Expert Witness Report of Juan G. Santiago Regarding Lack of Written Description, Non-Enablement, and Indefiniteness of the Asserted Claims of U.S. Patent Nos. 5,421,823; 5,324,422; 5,438,510; and 5,431,626, Apr. 24, 2009.
Opening Expert Witness Report of Dr. Martin Roberts Regarding a History of Peritoneal Dialysis and the Obviousness and Consequent Invalidity of the Asserted Claims of U.S. Patent No. 5,421,823, Apr. 24, 2009.
Opening Expert Witness Report of Dr. Darrell Long Regarding Technical Features of the High Flow Peritoneal Dialysis and Personal Cycler Machines, Apr. 24, 2009.
Defendants' Preliminary Invalidity Contentions for U.S. Patent No. 5,421,823, *Baxter Healthcare Corporation* v. *Fresenius Medical Care Holdings*, Case No. C 07-01359 PJH (JL), filed Aug. 24, 2007.
Defendants' Supplemental Invalidity Contentions for U.S. Patent No. 5,421,823, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 6,503,062, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 6,808,369, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 5,324,422, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 5,438,510, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 6,814,547, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 5,431,626, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 6,929,751, *Baxter Healthcare Corporation* v. *Fresenius Medical Care Holdings*, Case No. C 07-01359 PJH (JL), filed Jan. 31, 2008.
Defendants' Preliminary Invalidity Contentions for U.S. Patent No. 7,083,719, *Baxter Healthcare Corporation* v. *Fresenius Medical Care Holdings*, Case No. C 07-01359 PJH (JL), filed Jan. 31, 2008.
Defendants' Final Invalidity Contentions for U.S. Patent No. 6,814,547, *Baxter Healthcare Corporation* v. *Fresenius Medical Care Holdings*, Case No. C 07-01359 PJH (JL), filed Apr. 1, 2009.
Fresenius 90/2 Peritoneal Therapy Cycler (on information and belief, on sale in United States by 1991).
Blumenkrantz et al., Applications of the Redy Sorbent System to Hemodialysis and Peritoneal Dialysis, Artificial Organs, vol. 3, No. 3 (Aug. 1979).
Blumenkrantz et al., Development of a Sorbent Peritoneal Dialysate Regeneration System—A Progress Report, European Dialysis and Transplant Association 1978.
Blumenkrantz and Roberts, Progress in Peritoneal Dialysis: a Historical Prospective, Contributions to Nephrology, vol. 17, pp. 101-10 (1979).
Diaz-Buxo, CCPD is even better than CAPD, Kidney International, vol. 28, Suppl. 17, pp. S-26-S-28 (1985).
Diaz-Buxo, CCPD Technique and Current Clinical Experience (1982).
Diaz-Buxo, et al., Continuous Cyclic Peritoneal Dialysis: A Preliminary Report, Artificial Organs, vol. 5, No. 2, pp. 157-161 (May 1981).
Diaz-Buxo, Current Status of Continuous Cyclic Peritoneal Dialysis (CCPD), Peritoneal Dialysis International, vol. 9, pp. 9-14 (1989).
Diaz-Buxo, Issues in Nephrology: Continuous Cyclic Peritoneal Dialysis, NAPHT News, Feb. 1983, pp. 12-14.
Diaz-Buxo, Peritoneal Dialysis Reverse Osmosis Machines and Cyclers, Dialysis Therapy, pp. 41-48 (1986).
Drukker et al., Replacement of Renal Function by Dialysis, 2nd Ed., Ch. 21, 1983.
Lewin and Maxwell, Sorbent-Based Regenerating Peritoneal Dialysis, Sorbents and Their Clinical Applications, pp. 353-374 (1980).
Lewin et al., Sorbent for Application in the Treatment of ESRD Patients, Annual Progress Report re Contract #N01-AM-9-2215, submitted Jun. 22, 1982.
Ratnu, et al., A New Technique—Semicontinuous Rapid Flow, High Volume Exchange—for Effective Peritoneal Dialysis in Shorter Periods, Nephron, vol. 31, pp. 159-63 (1982).
Twardowski, Peritoneal Dialysis: Current Technology and techniques, Postgraduate Medicine, vol. 85, No. 5 (Apr. 1989).
Product Evaluation Reports: Peritoneal Dialysis Machine "Pac-X," Hospital Materials Management, vol. 12, No. 11, p. 16 (Nov. 1987).
Brochure entitled, AP Hauni: Automatisches Peritonealdialyse-Great (1970).
Brochure entitled, Fresenius Delivers 90/2 Peritoneal Therapy Cycler.
Brochure entitled, REDY Universal Re-circulating Dialysate System.
Brochure entitled, SIF 901 Perugia.
Translation of brochure entitled, SIF 901 Perugia.
Translation of Certificate for translation of brochure entitled, SIF 901 Perugia.
Operators Instructions for Fresenius 90/2 Peritoneal Therapy Cycler.
Photo of dialysis patient connected to machine.
Photo of dialysis machine.
Peritoneal Dialyser PD700 Service Manual, Jun. 1977.
Peritoneal Dialyser PD700 Instruction Manual.
PD700 Peritoneal Dialyser Users Hand-book, Dec. 1977.
Operating Instructions, Peritoneal Dialyser PD700, For Ser. No. 300.
Brochure entitled, Peritoneal Dialyser PD700, May 1979.
Brochure entitled, for Volume Measurement, Temperature Control and Cycling of Dialysing Fluid, Peritoneal Dialyser PD700, 1970.
Skotselanvisning for Peritoneal—Dialysapparat PD700.
Bergstrom et al., An Automated Apparatus for Peritoneal Dialysis with Volumetric Fluid Balance Measurement, reprinted from Dialysis & Transplantation, Jun./Jul. 1976.
U. Callsen, Peritoneal-Dialysator PD700, Prakt. Anasth. 9 (1974).
Piazolo et al., Erfahrungen mit einem neuen vollautomatsischen Paritonenal-dialysegerat, Munchener Medizinische Wochenschrift, 1972.
Technical Note, PD700 Peritoneal Dialyser, Jan. 29, 1979.
Assorted Photos of dialysis machine with and without casing on.
Elsevier Science Ltd., Air-Operated Diaphragm Pumps, World Pumps, Jan. 1996, at 38.

Bran & Luebbe GmbH, Diaphragm Metering Pumps, Chem. Eng'g Progress, Apr. 1987, at 18-24.

M. Schalbach, E.S. Bucherl & O. Franke, An Electronically Controlled Implantable Auxiliary Ventricle, published in Advances in Biomedical Engineering and Medical Physics: Cardiac Engineering, vol. 3.

Gene L. Mrava, Mock Circulation Systems for Artificial Hearts, published in Advances in Biomedical Engineering and Medical Physics: Cardiac Engineering, vol. 3.

W.M. Phillips, J.A. Brighton & W.S. Pierce, Artificial Heart Evaluation Using Flow Visualization Techniques, published in Transactions: American Society for Artificial Internal Organs, vol. XVIII (1972).

J.A. Brighton, W.S. Pierce, D.Landis & G. Rosenberg, Measuring Cardiac Output of Pneumatically Driven Total Artificial Hearts, published in 30th Anniversary Conference on Engineering in Medicine and Biology: Proceedings, vol. 19 (Nov. 5-9, 1977).

Operator's Instructions, Fresenius 90/2 Peritoneal Therapy Cycler (Rev. C. copyright 1991-2000).

Memorandum of Donald X. Vaccarino entitled 90/2 History File (1991-1992).

Document entitled 90/2 Cycler Software, Version 3.96 (Jan. 24, 1992).

Software Change Requests (Jul. 8, 1991-Oct. 3, 1992).

Brochure entitled Fresenius Delivers 90/2 Peritoneal Therapy Cycler (Apr. 2001).

90/2 Quick Reference.

90/2 Cycler Parts List (Nov. 6, 1997).

90/2 Cycler Box Contents.

90/2 Brochure (Jul. 1993).

90/2 Brochure (Apr. 2001).

90/2 Directions for Use.

90/2 Document Index.

Freedom Cycler Document Index.

Specification entitled Inpersol Cycler 3000 Operating Manual, List No. 21952-04, dated 1990.

Training aid entitled Learning to Use the Inpersol Cycler 3000, dated Jul. 1991.

Fresenius USA/Delmed 90/2 Peritoneal Dialysis System Operators Manual, dated Feb. 6, 1991.

Fresenius 90/2 Peritoneal Therapy Cycler Operator's Instructions, dated 2000.

Fresenius 90/2 PD Cycler Set Patient Information Card.

Fresenius Freedom Cycler Operating Instructions.

Non-final Office Action for U.S. Appl. No. 11/617,527 dated Nov. 24, 2008.

Final Office Action for U.S. Appl. No. 11/617,527 dated May 5, 2009.

Non-final Office Action for U.S. Appl. No. 11/617,527 dated Aug. 12, 2009.

Non-final Office Action for U.S. Appl. No. 11/614,850 dated May 14, 2009.

Non-Final Office Action for U.S. Appl. No. 10/155,754 mailed Sep. 11, 2003.

Final Office Action for U.S. Appl. No. 10/155,754 mailed Mar. 24, 2004.

Final Office Action for U.S. Appl. No. 11/614,850 mailed Mar. 18, 2010.

Non-Final Office Action for U.S. Appl. No. 11/614,858 mailed May 13, 2010.

Final Office Action for U.S. Appl. No. 11/617,527 mailed Jan. 21, 2010.

Non-Final Office Action for U.S. Appl. No. 11/617,527 mailed Jul. 16, 2010.

Non-Final Office Action for U.S. Appl. No. 10/446,068 mailed May 12, 2006.

Final Office Action for U.S. Appl. No. 10/446,068 mailed Nov. 7, 2006.

Non-Final Office Action for U.S. Appl. No. 10/446,068 mailed Sep. 7, 2007.

Final Office Action for U.S. Appl. No. 10/446,068 mailed Feb. 28, 2008.

Final Office Action for U.S. Appl. No. 10/446,068 mailed Jul. 31, 2008.

Non-Final Office Action for U.S. Appl. No. 10/446,068 mailed Nov. 14, 2008.

Non-Final Office Action for U.S. Appl. No. 11/773,787 mailed Jul. 28, 2010.

Non-Final Office Action for U.S. Appl. No. 12/506,738 mailed Jun. 24, 2011.

Non-Final Office Action for U.S. Appl. No. 12/903,902 mailed Jul. 6, 2011.

Non-Final Office Action for U.S. Appl. No. 12/903,887 mailed Jul. 6, 2011.

Non-Final Office Action for U.S. Appl. No. 11/773,148 mailed May 17, 2010.

Final Office Action for U.S. Appl. No. 11/773,148 mailed Feb. 7, 2011.

Non-Final Office Action for U.S. Appl. No. 12/408,432 mailed Mar. 3, 2011.

Non-Final Office Action for U.S. Appl. No. 12/987,738 mailed Apr. 29, 2011.

\* cited by examiner

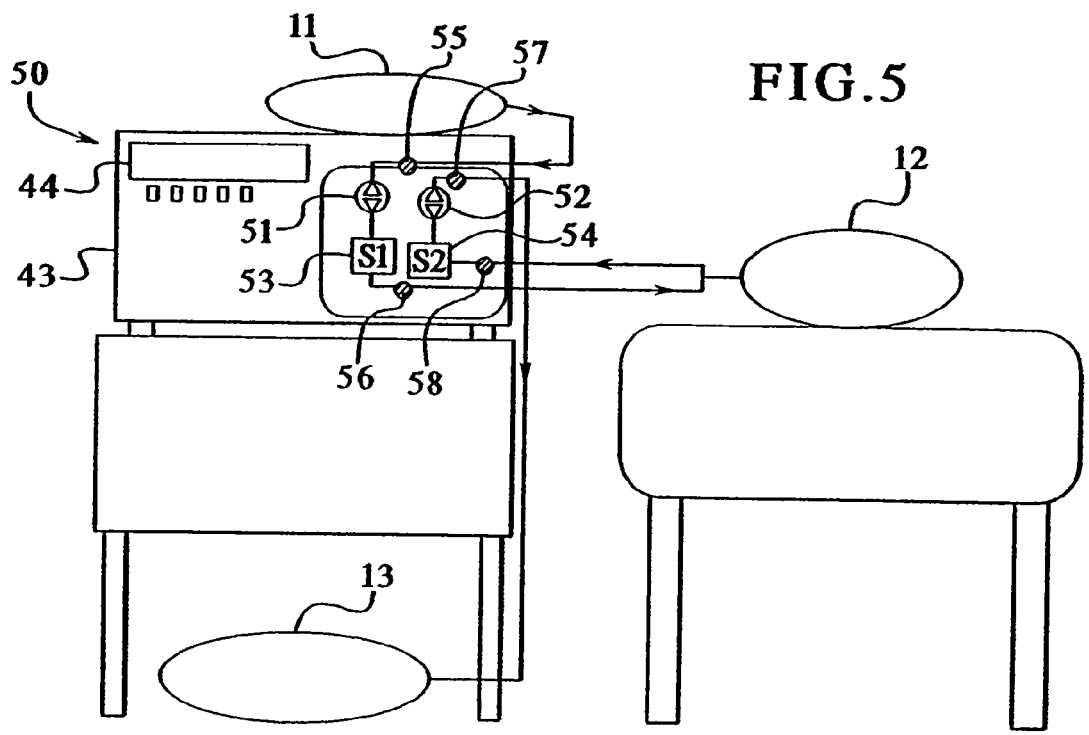
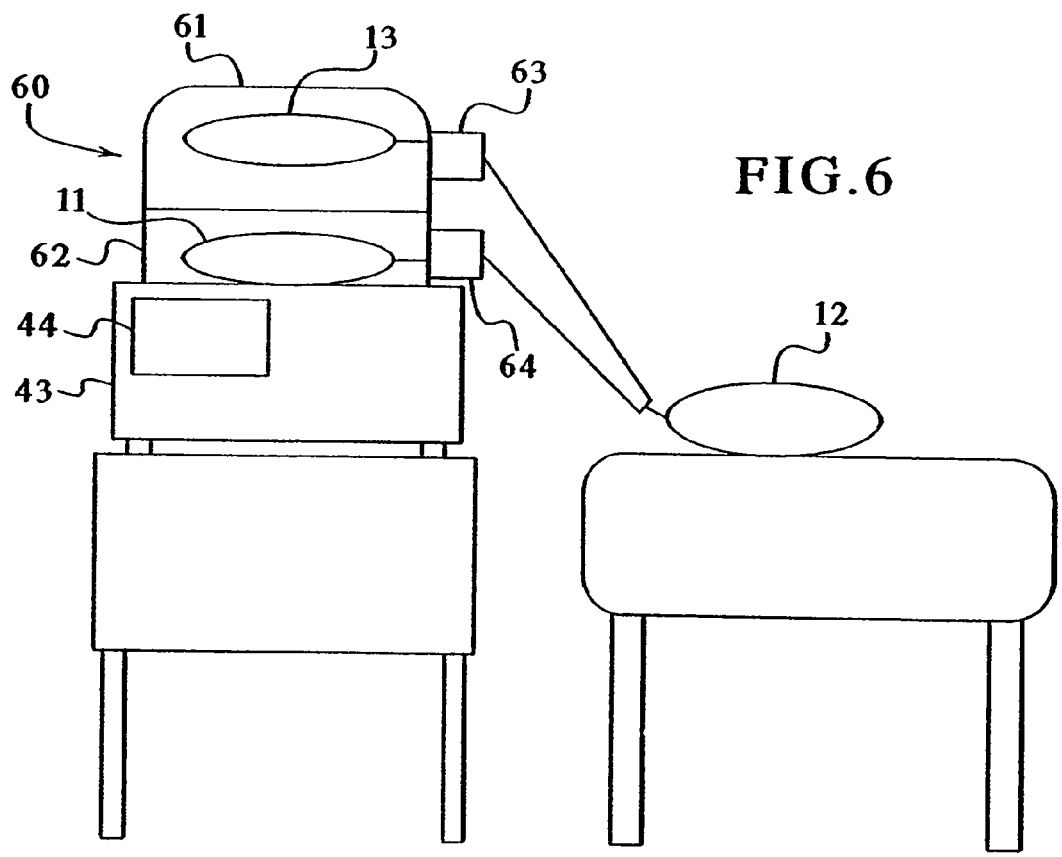

METHOD AND APPARATUS FOR MONITORING AND CONTROLLING PERITONEAL DIALYSIS THERAPY

PRIORITY CLAIM

This application is a continuation of U.S. patent application Ser. No. 10/446,068, filed May 27, 2003, entitled "Method And Apparatus For Monitoring And Controlling Peritoneal Dialysis Therapy," which is a divisional application of U.S. patent application Ser. No. 10/078,568, filed Feb. 14, 2002, having the same title as above, issued as U.S. Pat. No. 6,592,542, which is a continuation of U.S. patent application Ser. No. 09/501,778, filed Feb. 10, 2000, having the same title as above, issued as U.S. Pat. No. 6,497,676. Both disclosures are hereby incorporated by reference herein.

BACKGROUND

The present invention relates generally to the treatment of end stage renal disease. More specifically, the present invention relates to methods and apparatus for monitoring the performance of peritoneal dialysis.

Using dialysis to support a patient whose renal function has decreased to the point where the kidneys no longer sufficiently function is known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, certain inherent disadvantages exist with hemodialysis.

To overcome the disadvantages associated with hemodialysis, peritoneal dialysis was developed. Peritoneal dialysis utilizes the patient's own peritoneum as a semi-permeable membrane. The peritoneum is a membranous lining of the abdominal body cavity. Due to good perfusion, the peritoneum is capable of acting as a natural semi-permeable membrane.

Peritoneal dialysis periodically infuses sterile aqueous solution into the peritoneal cavity. This solution is called peritoneal dialysis solution, or dialysate. Diffusion and osmosis exchanges take place between the solution and the blood stream across the natural body membranes. These exchanges remove the waste products that the kidneys normally excrete. The waste products typically consist of solutes like urea and creatinine. The kidneys also maintain the levels of other substances such as sodium and water which need to be regulated by dialysis. The diffusion of water and solutes across the peritoneal membrane during dialysis is called ultrafiltration.

In continuous ambulatory peritoneal dialysis, a dialysis solution is introduced into the peritoneal cavity utilizing a catheter. An exchange of solutes between the dialysate and the blood is achieved by diffusion. Further removal is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter.

Peritoneal dialysis raises a number of concerns including: the danger of peritonitis; a lower efficiency and therefore increased duration of dialysis hours compared to hemodialysis; and costs incurred when automated equipment is utilized.

A number of variations on peritoneal dialysis have been explored. One such variation is automated peritoneal dialysis ("APD"). APD uses a machine, called a cycler, to automatically infuse, dwell, and drain peritoneal dialysis solution to and from the patient's peritoneal cavity. APD is particularly attractive to a peritoneal dialysis patient, because it can be performed at night while the patient is asleep. This frees the patient from the day-to-day demands of continuous ambulatory peritoneal dialysis during his/her waking and working hours.

The APD sequence typically lasts for several hours. It often begins with an initial drain cycle to empty the peritoneal cavity of spent dialysate. The APD sequence then proceeds through a succession of fill, dwell, and drain phases that follow one after the other. Each fill/dwell/drain sequence is called a cycle. APD can be and is practiced in a number of different ways.

Current APD systems do not monitor the patient intraperitoneal pressure during a therapy session. Current systems simply limit the external pressure (or suction) that a pump can apply to the line or lumen that is attached to the patient catheter. If the patient is located below the system, sometimes referred to as a cycler, a gravity head will add to the positive fill pressure that the cycler can apply to the patient catheter. Conversely, if the patient is located above the cycler, the gravity head will decrease from the positive fill pressure that the cycler can apply to the patient catheter.

The monitoring of intraperitoneal pressure would be useful because cyclers will sometimes not fully drain a patient between cycles. Specifically, currently-available cyclers are unable to determine whether a patient absorbed some fluid or whether some fluid is simply not able to be drained out because of the position of the patient or the catheter.

As a result, some currently-available systems utilize a minimum drain threshold to determine the amount of fluid that should be delivered to the patient during the next fill. For example, if 85% of the fill volume has been drained when the cycler determines that the patient is "empty", the next fill volume will be 100%. If only 80% were drained, the next fill volume would be limited to 95%.

A negative ultrafiltrate (uF) alarm will sound when the patient has retained more than a predetermined percentage of the fill volume. The predetermined percentage can typically be either 50% or 100% of the fill volume. However, the patient can override this alarm if he/she does not feel overfull. The number of times the patients can override the uF alarm during a single therapy may be limited by the software of the cycler. However, the uF alarm typically does not consider the actual ultrafiltrate that may also accumulate in the peritoneal cavity along with the dialysate.

Currently-available cyclers fill the patient to a specific, preprogrammed volume during each cycle. The doctor prescribes this fill volume based upon the patient's size, weight and other factors. However, because currently-available cyclers cannot monitor intraperitoneal pressure, the doctor cannot take this factor into account when formulating the prescription. It is also known that intraperitoneal pressure (IPP) has an effect on ultrafiltration (UF).

FIGS. 1-3 provide schematic illustrations of current APD cyclers. None of them attempt to monitor intraperitoneal pressure.

Referring to FIG. 1, a cycler 10a is illustrated which includes a dialysate container 11, a patient 12 and a drain container 13 are illustrated schematically. The infusion of dialysate from the container 11 into the patient 12 is caused by the gravitational head indicated at 14 while the draining of used dialysate from the patient 12 to the drain container 13 is caused by the drain head indicated at 15. The cycler 10a includes no sensors for monitoring the pressure inside the peritoneum of the patient 12. A single lumen 16 connects both the dialysate container 11 and drain container 13 to the patient 12. Valves 17, 18 operated by the cycler 10a control the flow of either dialysate from the container 11 to the patient 12 or waste material from the patient 12 to the drain container 13.

Turning to FIG. 2, in the cycler 10b, the drain container 13 and dialysate container 11 are contained within a pressurized chamber 19. The chamber 19 can be pressurized or evacuated to either fill or drain the patient. Again, the selective operation of valves 17, 18 control whether dialysate is being transferred to or from the patient 12. Again, no sensors are provided for detecting or monitoring intraperitoneal pressure of the patient 12.

Turning to FIG. 3, in the system 10c, a dialysate container 11 is connected to a pump 21 which, in turn, connects the dialysate container 11 to a common lumen or catheter 16 which is connected to the patient. A fluid flow control valve is provided at 23 and is controlled by the cycler 10c. The drain container 13 is also connected to a pump 24 which, in turn, connects the drain container 13 to the lumen 16. A control valve is again provided at 25.

The drain and fill rates of the cyclers 10a-10c illustrated in FIGS. 1-3 are determined by the gravitational head (see FIG. 1) or the suction or pressure (see FIGS. 2 and 3) applied to the patient line 16. Typically, the cyclers 10a-10c fail to optimize either the fill rate or the drain rate because the pressure is either fixed by the gravitational head or the pressure or suction applied by the chamber 10b of FIG. 2 which occurs at the opposing end of the patient line 16. Thus, without measuring the intraperitoneal pressure or having a way to estimate the same, it is difficult to optimize either the drain or fill rate. In the case of the cycler 10c in FIG. 3, optimizing the drain or fill rate is guesswork due to the lack of any pressure reading at all.

Accordingly, there is a need for an improved cycler that measures patient intraperitoneal pressure during a therapy session, including both during the drain and the fill as well as the dwell. Further, there is a need for an improved cycler that measures intraperitoneal pressure and which would use that data to more completely drain a patient between cycles. Further, there is a need for an improved cycler which would accurately measure intraperitoneal pressure to avoid overfilling a patient. Finally, there is a need for an improved cycler which would monitor intraperitoneal pressure during both the fill and drain cycles to optimize the speed at which the patient is filled and drained and to therefore increase the dwell portion of a therapy session.

SUMMARY

The present invention satisfies the aforenoted needs by providing a system for providing peritoneal dialysis to a patient which comprises a dialysate container connected to the patient with a first pressure sensor connected in-line herebetween, and a drain container connected to the patient with a second pressure sensor connected in-line therebetween.

In an embodiment, the system further comprises a first pump disposed in-line between the dialysate container and the first pressure sensor.

In an embodiment, the dialysate flows from the dialysate container into the patient under a hydrostatic head.

In an embodiment, a second pump is disposed in-line between the drain container and the second pressure sensor.

In an embodiment, the dialysate flows from the patient to the drain container under a hydrostatic head.

In an embodiment, the second pressure sensor measures an intraperitoneal pressure of the patient while dialysate flows from the dialysate container to the patient.

In an embodiment, the first pressure sensor measures an intraperitoneal pressure of the patient while dialysate flows from the patient to the drain container.

In an embodiment, the system further comprises a first lumen connecting the dialysate container to the first sensor and the first sensor to a catheter, and a second lumen connecting the drain container to the second sensor and the second sensor to the catheter, the catheter being connected to the patient, a flow of dialysate from the patient to the drain container evacuating dialysate from the first lumen and causing said dialysate from the first lumen to flow through the second lumen and to the drain container.

In an embodiment, the catheter is a dual lumen catheter.

In an embodiment, the first and second sensors are redundant in-line pressure/vacuum sensors.

In an embodiment, the present invention provides a method for dialyzing a patient comprising the steps of: placing a catheter in a peritoneum of the patient; providing at least one dialysate container; connecting the dialysate container to the catheter with a first lumen that includes a first pressure sensor disposed in-line and between the catheter and the dialysate container; providing at least one drain container; connecting the drain container to the catheter with a second lumen that includes a second pressure sensor disposed in-line and between the catheter and the drain container; transferring dialysate from the dialysate container to the peritoneum of the patient and monitoring an intraperitoneal pressure of the patient with the second pressure sensor; and transferring dialysate from the peritoneum of the patient to the drain container and monitoring the intraperitoneal pressure of the patient with the first pressure sensor.

In an embodiment, the step of transferring dialysate from the dialysate container to the peritoneum of the patient further comprises pumping dialysate from the dialysate container to the patient with a first pump disposed in-line between the dialysate container and the first pressure sensor.

In an embodiment, the step of transferring dialysate from the peritoneum of the patient to the drain container further comprises pumping dialysate from the peritoneum of the patient to the drain container with a second pump disposed in-line between the drain container and the second pressure sensor.

In an embodiment, the dialysate container is disposed vertically above the peritoneum of the patient and the step of transferring dialysate from the dialysate container to the peritoneum of the patient further comprises flowing dialysate from the dialysate container to the patient under a hydrostatic head.

In an embodiment, the drain container is disposed vertically below the peritoneum of the patient and the step of transferring dialysate from the peritoneum of the patient to the drain container further comprises flowing dialysate from the peritoneum of the patient to the drain container under a hydrostatic head.

Other objects and advantages of the invention will become apparent upon reading the following detailed description and appended claims, and upon reference to the accompanying drawings.

BRIEF DESCRIPTION OF THE FIGURES

FIG. 5 illustrates, schematically, a second embodiment of an automated peritoneal dialysis system made in accordance with the present invention;

FIG. 6 illustrates, schematically, a third embodiment of an automated peritoneal dialysis system made in accordance with the present invention;

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION

Figure 1:
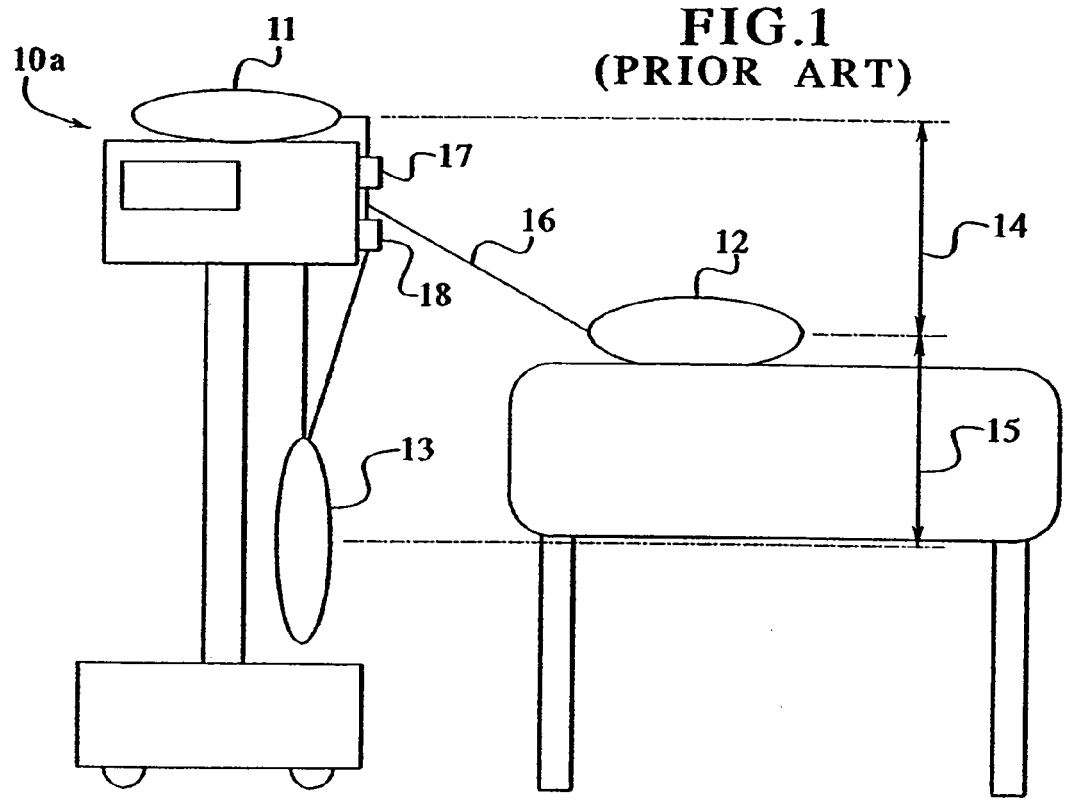
FIG. 1 illustrates, schematically, a prior art automated peritoneal dialysis system.
Figure 2:
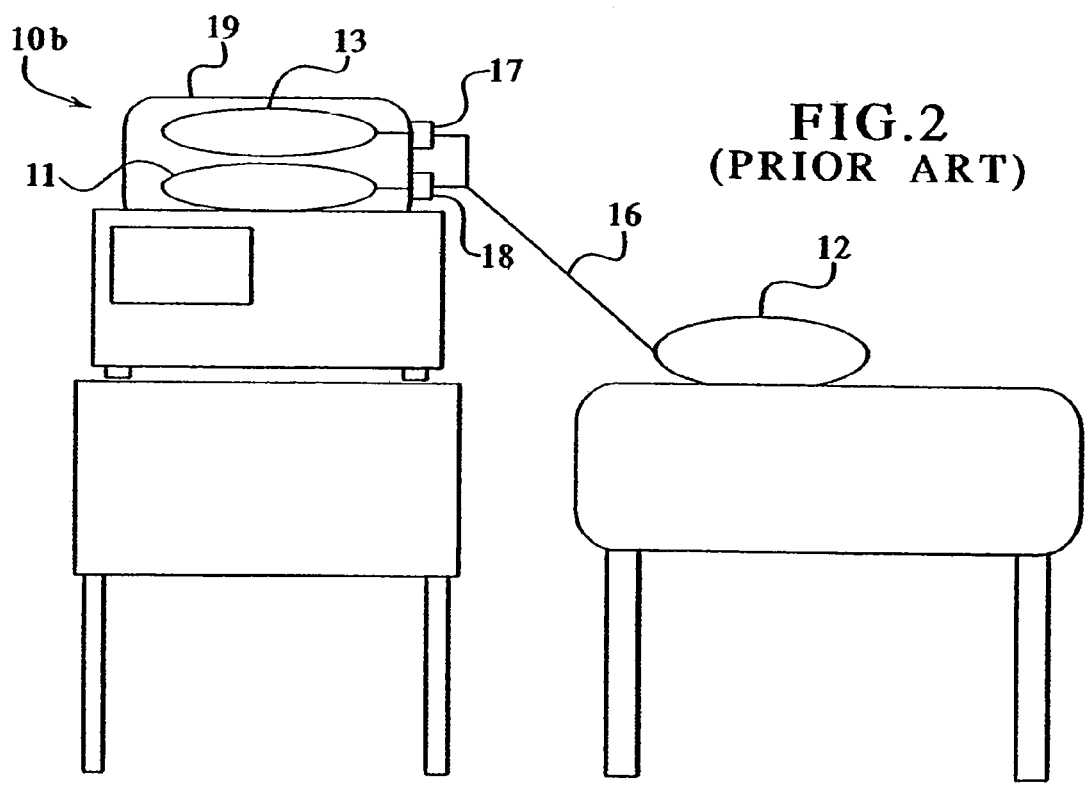
FIG. 2 illustrates, schematically, a prior art automated peritoneal dialysis system.
Figure 3:
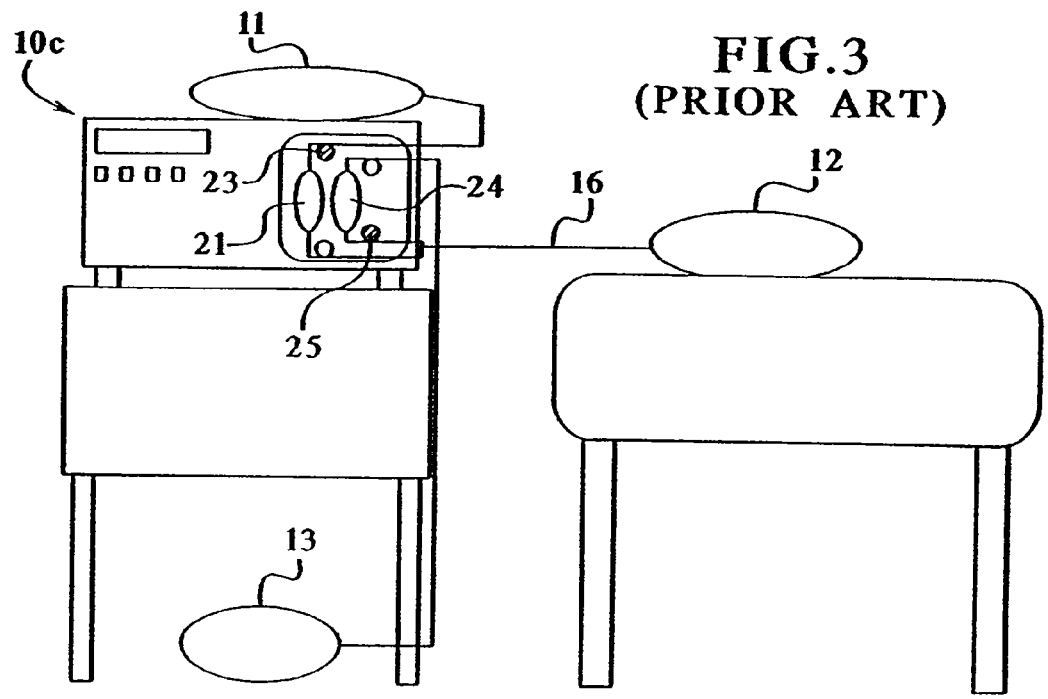
FIG. 3 illustrates, schematically, a prior art automated peritoneal dialysis system.
Figure 4:
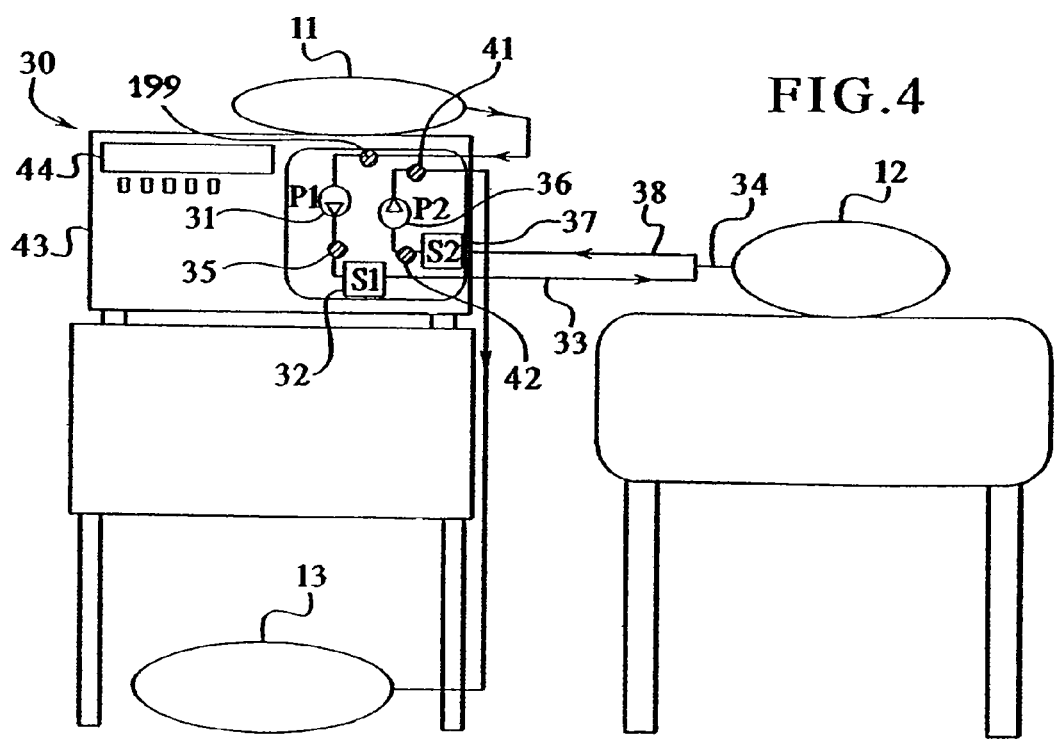
FIG. 4 illustrates, schematically, an automated peritoneal dialysis system made in accordance with the present invention.

Turning to FIG. 4, a cycler 30 includes a dialysate container 11 connected to a pump 31. The pump 31 is connected to a pressure sensor 32. The pump 31 and pressure sensor 32 are disposed in-line in a lumen 33 that connects the dialysate container 11 to a catheter 34. Control valves are provided at 35, 199. A drain container 13 is also connected to a pump 36 which is connected to a sensor 37. The pump 36 and sensor 37 are also connected in-line to a lumen 38 which connects the drain container 13 to the catheter 34. Control valves are again provided at 41, 42. During the fill, the pump 31 pumps dialystate from the container 11 through the lumen 33 and catheter 34 into the peritoneum (not shown) of the patient 12. During this time, the sensor 37 monitors and measures the intraperitoneal pressure. A signal is sent to the controller of the cycler 30 shown schematically at 43. A control panel is indicated generally at 44.

During the drain, the sensor 32 can accurately monitor and measure the intraperitoneal pressure of the patient 12. In the embodiment illustrated in FIG. 4, no pumps or control valves are disposed between the sensor 32 and the patient 12.

Turning to FIG. 5, a cycler 50 is illustrated which includes reversible pumping chambers 51, 52 with sensors 53, 54 disposed between the reversible pumping chambers 51, 52 and the patient 12 respectively. Control valves 55 and 56 are disposed on another side of the reversible pumping chamber 51 and the sensor 53 and control valves 57, 58 are provided on either side of the reversible pumping chamber 52 and sensor 54. The sensors 53, 54 actually measure the pressure on the diaphragms of the reversible pumping chambers 51, 52.

Turning to FIG. 6, a cycler 60 is illustrated with a chamber 61 for accommodating the drain container 13 and a chamber 62 for accommodating the dialysate container 11. Each chamber 61, 62 is equipped with an integrated valve assembly and pressure sensor shown at 63, 64. In the embodiment 60 shown in FIG. 6, the chamber 61 must be capable of being evacuated. Dialysate may flow from the dialysate container 11 by way of gravity or pressure fill. Again, the sensors of the valve assembly/sensor combinations 63, 64 monitor the intraperitoneal pressure of the patient 12 as discussed above.

Figure 7:
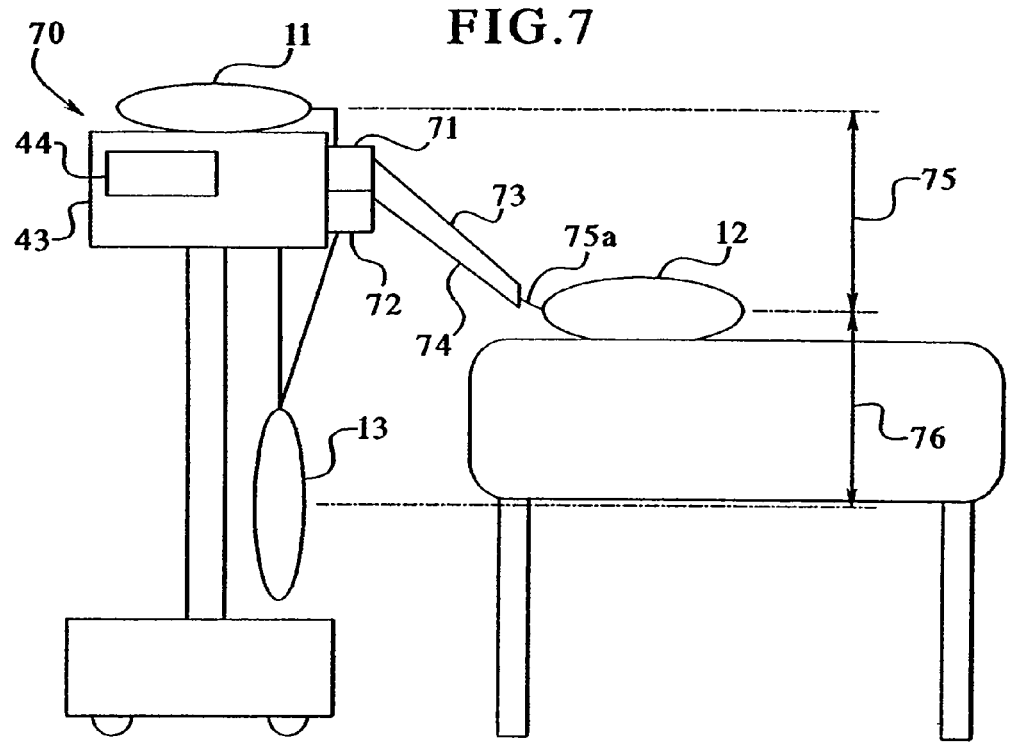
FIG. 7 illustrates, schematically, a fourth embodiment of an automated peritoneal dialysis system made in accordance with the present invention.

In the embodiment 70 illustrated in FIG. 7, the dialysate container 11 and drain container 13 are both connected to integrated control valves and pressure sensors 71, 72. Each of the integrated control valves and pressure sensors 71, 72 are connected to lumens 73, 74 respectively which are connected to the catheter 75a by way of a Y-connection. The details of all the Y-connections and clamps are not shown but are known to those skilled in the art. Flow from the dialysate container 11 to the patient is carried out under the gravitational head shown at 75 while flow from the patient to the drain container 13 is carried out under the gravitational head shown at 76.

Figure 8:
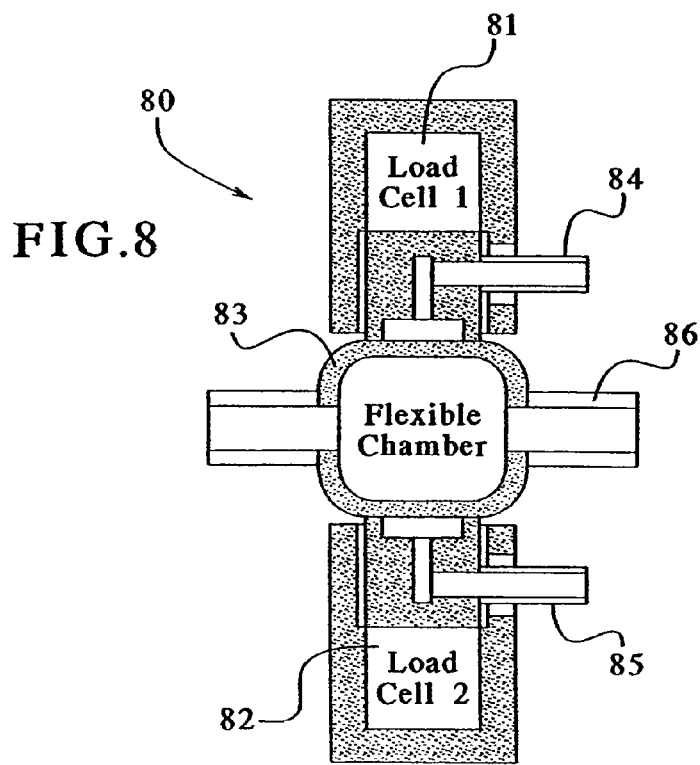
FIG. 8 illustrates a pressure sensor made in accordance with the present invention.

FIG. 8 illustrates one in-line pressure sensor 80 that is suitable for use with the present invention. Redundant load cells 81, 82 are connected to the flexible pressure sensing membrane 83 by a vacuum connected by the line 84, 85. A lumen connecting the cycler to the patient is shown at 86.

Figure 9:
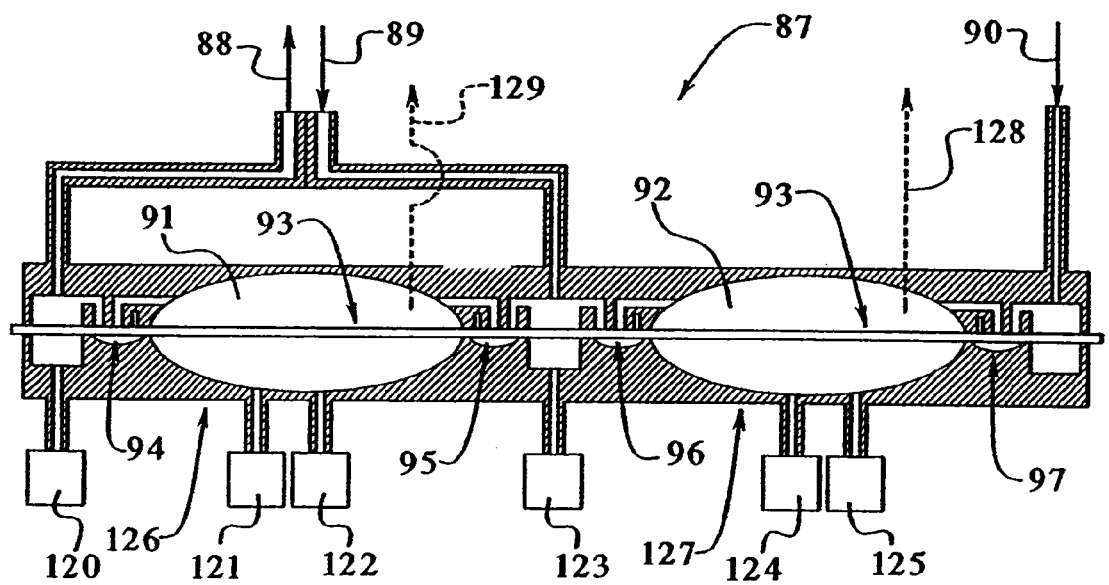
FIG. 9 illustrates a fifth embodiment incorporating dual pumping chambers and pressure sensors made in accordance with the present invention.

FIG. 9 illustrates a dual-pumping chamber cassette 87 which includes an output line 88 which connects the cassette 87 to the patient and an input line 89 connecting the patient to the cassette 87. The line 90 connects the cassette 87 to the dialysate container (not shown). Each pumping chamber 91, 92 are in communication with all three lines 88, 89 and 90. Thus, every line can be connected to either pumping chamber 91, 92. The pumping chambers 91, 92 are bound on one side by a common diaphragm shown at 93. Flow is controlled by the use of diaphragm valves shown at 94, 95, 96 and 97. Pressure sensors are shown at 120, 121, 122, 123, 124, 125. However, pressure sensors 123 and 120 are the sensors used to measure intraperitoneal pressure in accordance with the present invention. The remaining sensors 121, 122, 124, 125 are used to monitor the operation of the pumps 126, 127.

When the left diaphragm pump 126 is pushing dialysate to the patient, the sensor 123 can measure the intraperitoneal pressure through the line 89. When the left diaphragm pump 126 is draining fluid from the patient through the line 89, the sensor 120 can measure intraperitoneal pressure through the line 88 and while the right pump 127 is pumping fluid to the drain container (not shown) through the drain line shown schematically at 128. When the right diaphragm pump 127 is being used to drain fluid from the patient, the sensor 120 can measure intraperitoneal pressure while the left diaphragm pump 126 is pumping fluid to the drain container (not shown) through the drain line shown schematically at 129.

Figure 10:
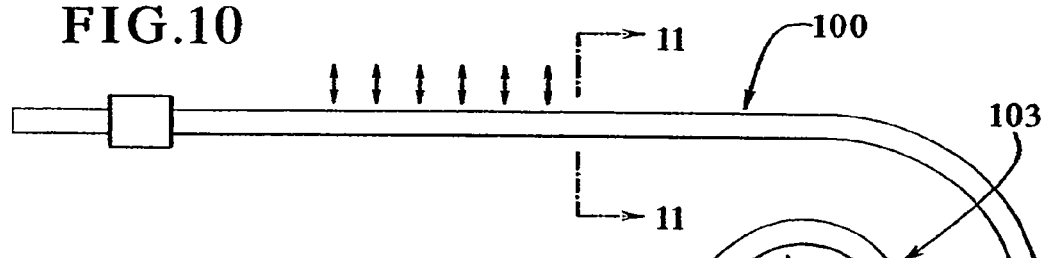
FIG. 10 illustrates, schematically, a dual lumen catheter that can be utilized with the present invention.
Figure 11:
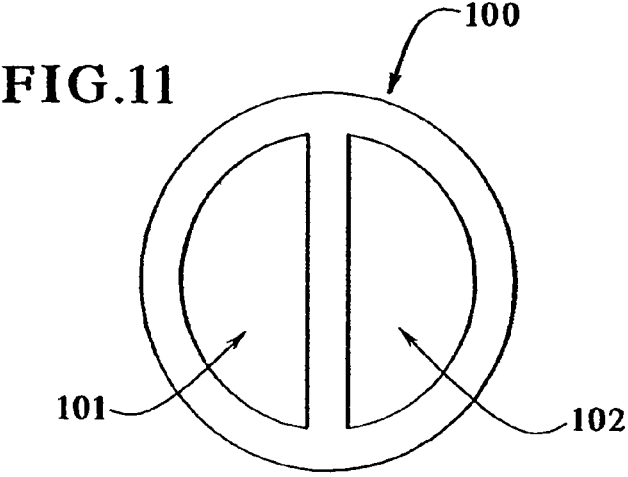
FIG. 11 is a sectional view taken substantially along line 11-11 of FIG. 10.

FIGS. 10 and 11 illustrate a dual-lumen catheter 100 which includes separate passageways 101, 102. The employment of a dual lumen catheter 100 as compared to a dual lumen patient line can move the point at which the pressure is measured to within the peritoneum itself by way of communication through the separate flowpaths 101, 102. The dual lumen catheter 100 installs like a single lumen catheter, yet will function either as a flow through or a standard catheter. Both fluid pathways 101, 102 are used to withdraw and deliver fluid during the drain and fill. While one pathway delivers fluid, the other pathway drains. The end section, shown generally at 103, is perforated.

A comparison of an APD therapy for a prior art APD cyclers and one manufactured in accordance with the present invention are summarized as follows:

| Therapy Parameter | Current APD Cycler | Cycler Using Invention |
|---|---|---|
| Total Therapy Volume | 15 liters | 15 liters |
| Fill Volume | 2.2 liters | 2.5 liters max |
| Fill Pressure Limit | not applicable | 14 mm Hg max |
| Total Therapy Time | 8 hours | 8 hours |
| Last (Day) Fill Volume | 1,500 ml | 1,500 ml |
| Last Fill Dextrose | Same | Same |
| Initial Drain Alarm | 1,200 ml | 1,200 ml |
| Drain X of N Alarm | 80% | 80% |

TABLE 1

Comparison of Therapies for Current Cyders versus Cycler using Invention Method

| Therapy Phase | Therapy Parameter | Prior Art Cycler 1 | Prior Art Cycler 2 | Invention Cycler 3 |
|---|---|---|---|---|
| Initial Drain | Drain Volume | 1,200 ml | 1,200 ml | 1,200 ml |
| | Patient Volume | 300 ml | 300 ml | 300 ml |
| Fill 1 of 5 | Fill Volume | 2,200 ml | 2,200 ml | 2,500 ml |
| | Patient Volume | 2,500 | 2,500 | 2,800 |
| | Fill Pressure | not applicable | not applicable | 12 mm Hg |
| Drain 1 of 5 | Drain Volume | 1,800 ml | 2,200 ml | 2,200 ml |
| | Patient Volume | 700 ml | 300 ml | 600 ml |
| Fill 2 of 5 | Fill Volume | 2,200 ml | 2,200 ml | 2,400 ml |
| | Patient Volume | 2,900 ml | 2,500 ml | 3,000 ml |
| | Patient Pressure | not applicable | not applicable | 14 mm Hg |
| Drain 2 of 5 | Drain Volume | 1,800 ml | 2,200 ml | 2,200 ml |
| | Patient Volume | 1,100 ml | 300 ml | 800 ml |
| Fill 3 of 5 | Fill Volume | 2,200 ml | 2,200 ml | 2,200 ml |
| | Patient Volume | 3,300 ml | 2,500 ml | 3,000 ml |
| | Patient Pressure | not applicable | not applicable | 14 mm Hg |
| Drain 3 of 5 | Drain Volume | 1,801 ml | 2,200 ml | 2,200 ml |
| | Patient Volume | 1,499 ml | 300 ml | 800 ml |
| Fill 4 of 5 | Fill Volume | 2,200 ml | 2,200 ml | 2,200 ml |
| | Patient Volume | 3,699 ml | 2,500 | 3.000 ml |
| | Patient Pressure | not applicable | not applicable | 3,000 ml |
| Drain 4 of 5 | I Drain Volume | 1,800 ml | 2,200 ml | 2,200 ml |
| | Patient Volume | 1,899 ml | 300 ml | 800 ml |
| Fill 5 of 5 | Fill Volume | uF Alarm Bypass 2,200 ml | 2,200 ml | 2,200 ml |
| Patient Volume | 4,099 ml | 2,500 ml | 3,00 ml | |
| | Patient Pressure | Patient Wakes Overfull, Manually Drains 1,500 ml | not applicable | 14 mm Hg |
| Drain 5 of 5 | Drain Volume | 1,800 ml | 2,200 ml | 2,200 ml |
| | Patient Volume | 799 ml | 300 ml | 800 ml |
| Final Fill | Fill Volume | 1,500 ml | 1,500 ml | 1,500 ml |

Inspection of Table 1 shows that cycler 1 woke the patient at around 4:30 in the morning with a negative uF alarm at the beginning of Fill 5. The patient bypassed the alarm because he did not feel overfull and immediately fell back asleep. He woke up about minutes later when he had difficulty breathing and felt extremely overfull. He manually drained about 1500 ml but was unable to go back to sleep. He filed a formal product complaint with the manufacturer.

The data of Table I shows that cycler 2 ran a completely normal therapy but the total therapy clearance (calculated based upon the sum of the night patient volumes) was only 84.5% of that obtained by cycler 3, which was using the cycler that used the method of the current invention.

The data of Table 1 shows that cycler 3 ran a completely normal therapy and that the fill volume was limited on one occasion by the maximum fill volume but on four occasions by the patient's intraperitoneal pressure. This patient never felt any discomfort and had no alarms during the night. The limit on the IPP prevented him from being overfilled even though he had successive drains that were not complete. The volume of fluid in his peritoneum never exceeded 3 liters.

The patient on cycler 1 had an intraperitoneal pressure in excess of 14 mm Hg during dwells 3 and 4. His breathing may have been impaired and his heart may have had to work harder but the discomfort was not enough to wake him up from a sound sleep until it peaked at 4,099 ml during dwell 5.

In conclusion, the method of the present invention provides for optimum fills and therefore more clearance while preventing overfills that bring discomfort and inhibit the function of vital body organs. A negative uF alarm would seldom occur because overfills of the required magnitude would be prevented by the IPP sensors.

CALCULATION OF INTRAPERITONEAL PRESSURE (IPP)

In order to calculate the IPP, one may first calculate the patient head height correction using conservation of energy:

$$\Delta(\tfrac{1}{2}\rho V^2 + P - pa_g h) + \text{Frictional Losses} = 0$$

The velocity V of fluid through the patient line is the same at both ends of the line as is the fluid density, so this equation can be written as $$(P_2 - P_1) - pa_g(h_2 h_1) + \text{Frictional Losses} = 0$$

which can be rearranged as $$\Delta h = \frac{(P_1 - P_2) - \text{Frictional Losses}}{\rho a_g}$$

EXAMPLE 1

P1=1.25 psig=85060 (gram/cm)/(cm$^2$-sec$^2$)
P2=0.9 psig=61240 (gram/cm)/(cm$^2$-sec$^2$)
Frictional Losses=39130 (gram/cm)/(cm$^2$-sec$^2$) with flow of 197 cm/min in a 4 mm ID line at a velocity of approximately 172 cm/sec, wherein
$a_g$=981 cm/sec$^2$
$\rho$=1 gram/cm$^3$ $$\Delta h = \frac{((85060 - 61240) - 39130)\,(\text{gram}/\text{cm})/(\text{cm}^2 - \text{sec}^2)}{1\,\text{gram}/\text{cm}*981\,\text{cm}/\text{sec}^2}$$

$\Delta h$=−15.6 cm (The patient is 15.6 cm below the membrane)

EXAMPLE 2

PI=1.25 psig=85060 (gram/cm)/(cm$^2$-sec$^2$) P2=0.45 psig=30620 (gram/cm)/(cm$^2$-sec$^2$)
Frictional Losses=39130 (gram/cm)/(cm$^2$-sec$^2$) with flow of 197 cmn/min in a 4 mm ID line at a velocity of approximately 172 cm/sec, wherein
$a_g$=981 cm/sec$^2$
$\rho$=1 gram/cm$^3$ $$\Delta h = \frac{((85060 - 30620) - 39130)\,(\text{gram}/\text{cm})/(\text{cm}^2 - \text{sec}^2)}{1\,\text{gram}/\text{cm}^3 * 981\,\text{cm}/\text{sec}^2}$$

$\Delta h$=+15.6 cm (The patient is 15.6 cm above the membrane)

The patient head height can be established at the beginning of each fill. Any changes in the head height that occur during the fill can be attributed to an increase in intraperitoneal pressure (IPP) since the patient is asleep.

Figure 12:
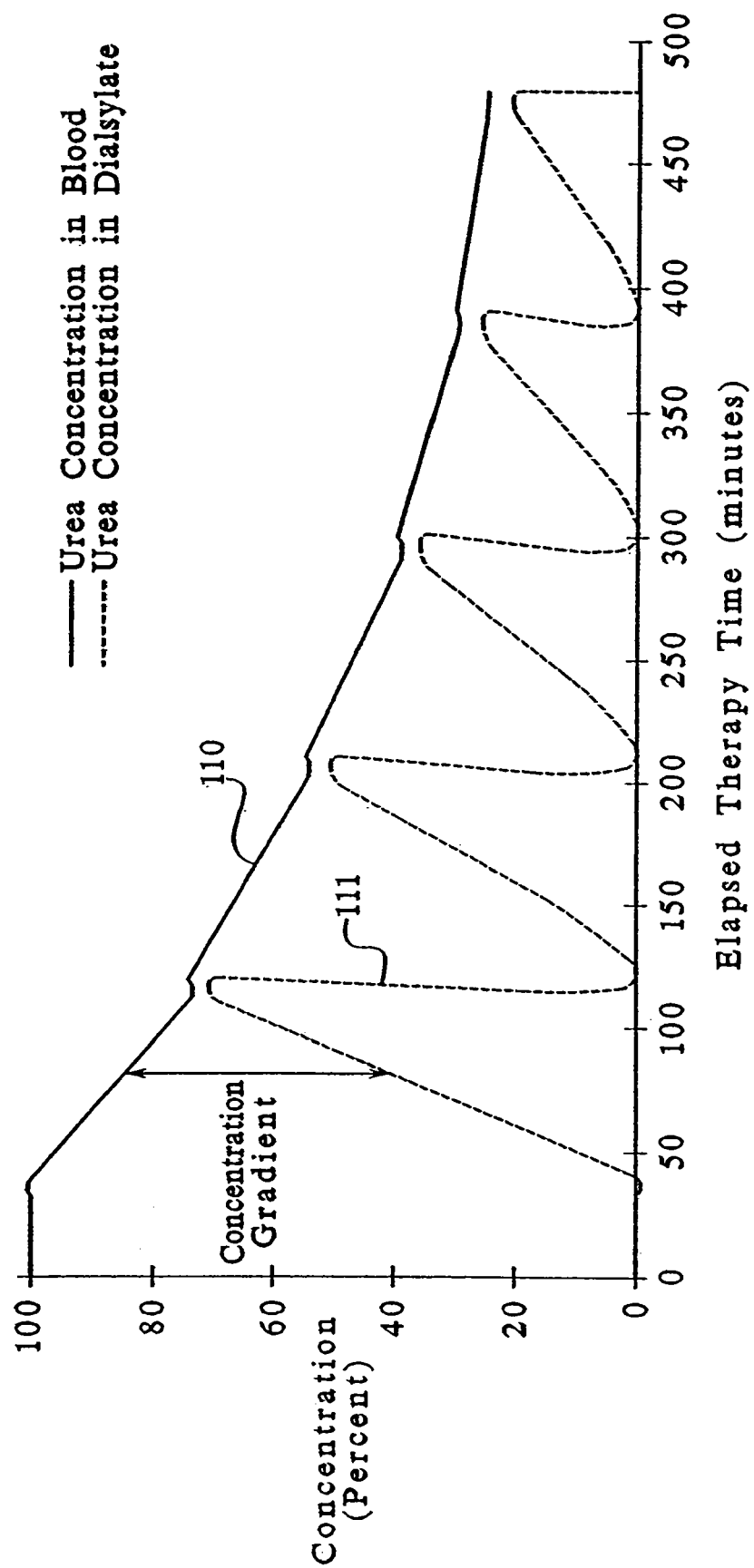
FIG. 12 illustrates, graphically, the urea concentration in blood and the urea concentration in a dialysate during a multiple dwell dialysis session.
Figure 13:
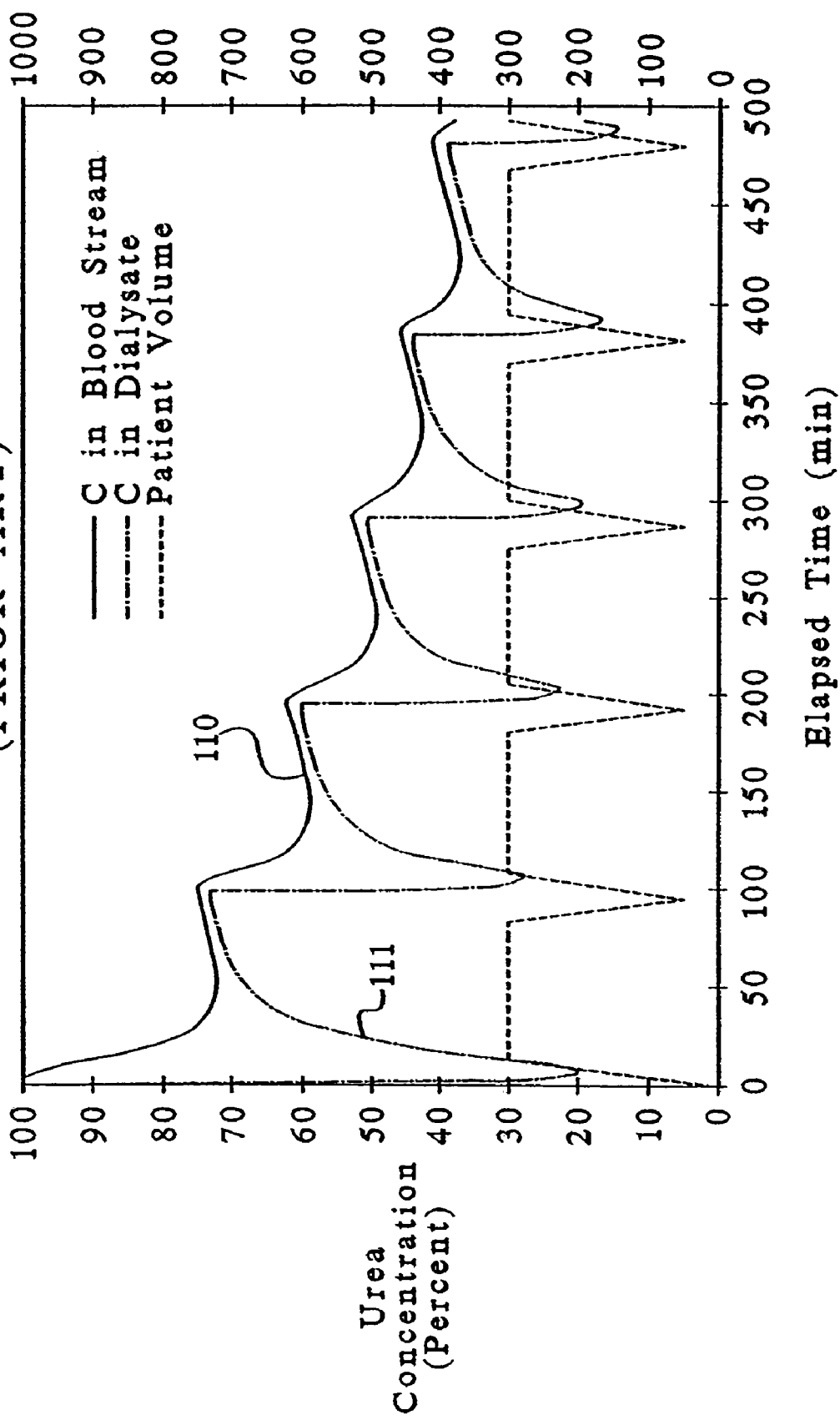
FIG. 13 illustrates, graphically, the concentration of urea in a patient's bloodstream versus the concentration of urea in a dialysate solution for an automated peritoneal dialysis solution practiced in accordance with the prior art.
Figure 14:
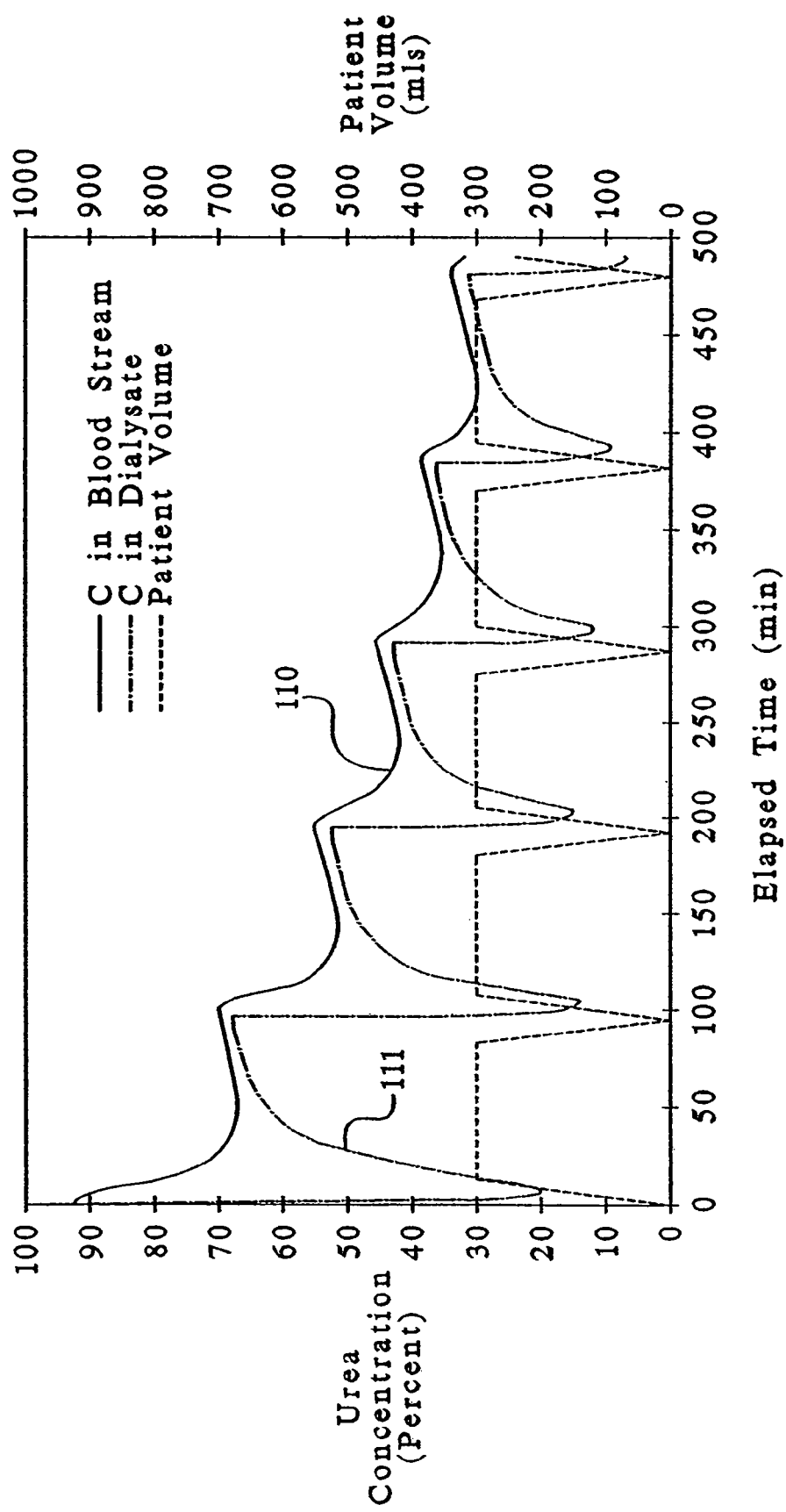
FIG. 14 illustrates, graphically, the concentration of urea in a patient's bloodstream versus the concentration of urea in a dialysate for an automated peritoneal dialysis therapy session carried out in accordance with the present invention.

Turning to FIG. 12, the concentration gradient between the urea concentration 110 in the patient's blood and the urea concentration 111 in the dialysate for typical APD cyclers is illustrated graphically. Comparing the results illustrated in FIGS. 13 and 14, it is evident that APD cyclers equipped with the sensors of the present invention provide superior results. Specifically, the data illustrated graphically in FIG. 13 was obtained using a prior art APD cycler. The data obtained in FIG. 14 was obtained using an APD cycler utilizing two sensors for monitoring intraperitoneal pressure. Note that the urea concentration 110 in the bloodstream is lower in FIG. 14 than in FIG. 13. Further note, the dialysate volume or fill volume is lower for the therapy illustrated in FIG. 14 than the therapy illustrated in FIG. 13. Thus, the present invention provides improved urea clearance with lower fill volumes.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

The invention claimed is:

1. A peritoneal dialysis system comprising:
a first pump actuator;
a second pump actuator;
first and second diaphragm pump chambers operable with the first and second pump actuators, respectively, each first and second pump chamber including a dialysis fluid compartment for receiving a dialysis fluid to be delivered to a patient line;
a pressure sensor located at a conduit upstream or downstream from one of the first and second pump chambers, the conduit in communication with the dialysis fluid compartment of the first or second pump chamber, the pressure sensor sensing a pressure of a dialysis fluid in the conduit, the patient line in fluid communication with the dialysis fluid compartment via the conduit, the conduit opened and closed via a dialysis fluid valve; and
wherein the system is configured to receive a signal from the pressure sensor and use the signal to modify a peritoneal dialysis treatment from a planned peritoneal dialysis treatment performed by the system to avoid an alarm condition.

2. The peritoneal dialysis system of claim 1, wherein the pressure sensor is positioned to sense the dialysis fluid pressure exerted on a diaphragm of the first pump chamber.

3. The peritoneal dialysis system of claim 1, which includes a second pressure sensor located at a second conduit and at a position upstream or downstream from the other of the first and second pump chambers, the second conduit in communication with the dialysis fluid compartment of the other pump chamber, the second conduit opened and closed via a second dialysis fluid valve.

4. The peritoneal dialysis system of claim 3, wherein the second pressure sensor is positioned to sense a pressure on a diaphragm of the second pump chamber.

5. The peritoneal dialysis system of claim 3, the patient line being a patient outlet line, and which includes a patient inlet line in fluid communication with the second fluid valve.

6. The peritoneal dialysis system of claim 1, which includes an additional fluid valve placed between the first pump chamber and a dialysate source.

7. A peritoneal dialysis system comprising:
a first diaphragm operated pump chamber;
a second diaphragm operated pump chamber;
a first pressure sensor positioned at a first conduit and upstream or downstream from the first pump chamber, the first conduit in communication with a dialysis fluid compartment of the first pump chamber, the first pressure sensor sensing a pressure of a dialysis fluid in the first conduit;
a second pressure sensor positioned at a second conduit upstream or downstream from the second pump chamber, the second conduit in communication with a dialysis fluid compartment of the second pump chamber, the second pressure sensor sensing a pressure of a dialysis fluid in the second conduit; and
wherein the system is configured to receive a signal from at least one of the pressure sensors and use the at least one signal to modify a peritoneal dialysis treatment from a programmed peritoneal dialysis treatment performed by the system to avoid an alarm condition.

8. The peritoneal dialysis system of claim 7, wherein the first and second pump chambers are configured for two-way pumping.

9. The peritoneal dialysis system of claim 7, wherein the fluid pressure exerted on one of the diaphragms and sensed by one of the sensors is a from-patient fluid pressure and the fluid pressure exerted on the other diaphragm and sensed by the other pressure sensor is a to-patient fluid pressure.

10. The peritoneal dialysis system of claim 7, wherein the first and second diaphragm operated pump chambers are part of a fluid cassette.

11. A peritoneal dialysis system comprising:
a dialysis fluid cassette including a diaphragm operated pump chamber;
a cycler positioned and arranged to apply a positive and a negative pressure to the diaphragm operated pump chamber;
a pressure sensor housed by the cycler and operating with the dialysis fluid cassette, wherein dialysis fluid before entering or after leaving the pump chamber flows through a conduit and across the pressure sensor; and
wherein the cycler is configured to receive a signal from the pressure sensor and use the signal to modify a treatment from a planned peritoneal dialysis treatment to ensure that a pressure of the fluid inside a patient ("IPP") does not exceed a pressure limit.

12. The peritoneal dialysis system of claim 11, which is configured to limit a fill volume to the patient based on the pressure limit.

13. The peritoneal dialysis system of claim 11, which is configured to allow the pump chamber to pump fluid to the patient until the IPP reaches the pressure limit.

14. The peritoneal dialysis system of claim 11, the cycler configured to relate IPP to a head height of the patient.

15. The peritoneal dialysis system of claim 11, the cycler configured to calculate a head height of the patient based on multiple signals from the pressure sensor.

16. A peritoneal dialysis system comprising:
a dialysis fluid cassette including diaphragm operated first and second pump chambers;
a first pressure sensor located downstream from the first pump chamber;
a second pressure sensor located upstream from the second pump chamber;
a dialysis fluid inlet port of the cassette in fluid communication with the first pump chamber;
a to-patient port of the cassette in fluid communication with the first pump chamber; and
wherein the first pressure sensor is located to sense dialysis fluid flowing between the dialysis fluid inlet port and the to-patient port and the second pressure sensor is located to sense dialysis fluid flowing into the second pump chamber; and
a cycler configured to use signals from the first and second pressure sensors to adjust a programmed peritoneal dialysis treatment to avoid an alarm condition.

17. The peritoneal dialysis system of claim 16, which includes a plurality of valves located between the dialysis fluid inlet port and the to-patient port, the first pressure sensor located to sense dialysis fluid flowing between the plurality of valves.

18. The peritoneal dialysis system of claim 17, wherein the plurality of valves each operate with a diaphragm of the cassette.

19. The peritoneal dialysis system of claim 16, wherein the first and second pressure sensors operate with a diaphragm of the cassette.

20. The peritoneal dialysis system of claim 1, wherein the conduit is part of a dialysis fluid cassette, the cassette including the first and second diaphragm pump chambers.

21. The peritoneal dialysis system of claim 7, wherein the first and second conduits are part of a dialysis fluid cassette.

22. The peritoneal dialysis system of claim 1, wherein the planned peritoneal dialysis treatment is modified to append a planned patient fill.

23. The peritoneal dialysis system of claim 7, wherein the programmed peritoneal dialysis treatment is modified to append a programmed patient fill.

24. The peritoneal dialysis system of claim 11, wherein the planned peritoneal dialysis treatment is modified to append a planned patient fill.

25. The peritoneal dialysis system of claim 16, wherein the programmed peritoneal dialysis treatment is adjusted to append a programmed patient fill.

\* \* \* \* \*